(12) United States Patent
Cantua

(10) Patent No.: US 11,198,012 B2
(45) Date of Patent: Dec. 14, 2021

(54) CATHODE-MINIMIZED STIMULATION PROGRAMMING

(71) Applicant: Medtronic, Inc., Minneapolis, MN (US)

(72) Inventor: Hector Cantua, Glen Allen, VA (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 16/339,310

(22) PCT Filed: Aug. 22, 2017

(86) PCT No.: PCT/US2017/047977
§ 371 (c)(1),
(2) Date: Apr. 3, 2019

(87) PCT Pub. No.: WO2018/067239
PCT Pub. Date: Apr. 12, 2018

(65) Prior Publication Data
US 2020/0046987 A1   Feb. 13, 2020

Related U.S. Application Data

(60) Provisional application No. 62/404,018, filed on Oct. 4, 2016.

(51) Int. Cl.
*A61N 1/36* (2006.01)
*A61N 1/372* (2006.01)
*A61N 1/05* (2006.01)
*A61N 1/06* (2006.01)

(52) U.S. Cl.
CPC ....... *A61N 1/37247* (2013.01); *A61N 1/0551* (2013.01); *A61N 1/06* (2013.01); *A61N 1/36071* (2013.01); *A61N 1/36171* (2013.01); *A61N 1/36175* (2013.01); *A61N 1/36185* (2013.01)

(58) Field of Classification Search
CPC .... A61N 1/37247; A61N 1/0551; A61N 1/06; A61N 1/36071; A61N 1/36171; A61N 1/36175; A61N 1/36185; A61N 1/36062; A61N 1/3606
See application file for complete search history.

(56) References Cited

U.S. PATENT DOCUMENTS

| 8,918,184 | B1 * | 12/2014 | Torgerson | A61N 1/36185 607/59 |
| 9,498,622 | B2 * | 11/2016 | King | A61N 1/0553 |
| 2004/0215288 | A1 | 10/2004 | Lee et al. | |
| 2004/0267330 | A1 * | 12/2004 | Lee | A61N 1/36082 607/48 |
| 2004/0267333 | A1 | 12/2004 | Kronberg | |

(Continued)

OTHER PUBLICATIONS

International Search Report and Written Opinion of International Application No. PCT/US2017/047977, dated Jan. 4, 2018, 11 pp.

(Continued)

*Primary Examiner* — Jennifer Pitrak McDonald
*Assistant Examiner* — Natasha Patel
(74) *Attorney, Agent, or Firm* — Shumaker & Sieffert, P.A.

(57) ABSTRACT

Programming a stimulator device to deliver a stimulation therapy at high-density parameter settings using a cathode-minimized electrode configuration determined to induce paresthesia over a patient pain pattern at low-density parameter settings.

21 Claims, 10 Drawing Sheets

(56) References Cited

U.S. PATENT DOCUMENTS

2011/0172737 A1     7/2011    Davis et al.
2015/0127062 A1*   5/2015    Holley ............... A61N 1/36132
                                                                    607/46

OTHER PUBLICATIONS

International Preliminary Report on Patentability from International Application No. PCT/US2017/047977, dated Apr. 9, 2019, 8 pp.
Sharan et al., "Evolving patterns of spinal cord stimulation in patients implanted for intractable low back and leg pain," Neuromodulation;5(3), Jul. 2002,13 pp.
Sato et al., "Spinal cord stimulation reduces hypersensitivity through activation of opioid receptors in a frequency-dependent manner," Eur J Pain;17(4), Apr. 2013, pp. 551-561.
Gao et al., "Effects of spinal cord stimulation with "standard clinical" and higher frequencies on peripheral blood flow in rats," Brain Res. 1313: Feb. 2010, pp. 53-61.
Shechter et al., "Conventional and kilohertz-frequency spinal cord stimulation produces intensity- and frequency-dependent inhibition of mechnical hypersensitivity in a rat model of neuropathic pain," Anesthesiology 119(2): Aug. 2013; pp. 422-432.
Song et al., "Efficacy of kilohertz-frequency and conventional spinal cord stimulation in rat models of different pain conditions," Neuromodulation 17(3): Jan. 2014, pp. 226-235.
De Ridder et al., "Burst Spinal Cord Stimulation for Limb and Back Pain," World Neurosurgery 80(5): Nov. 2013, pp. 642-649.
De Ridder et al., "Burst Spinal Cord Stimulation: Toward Paresthesia-Free Pain Suppression," Neurosurgery 66(5): May 2010, pp. 986-990.
Al-Kaisy et al., "Sustained effectiveness of 10 kHz high-frequency spinal cord stimulation for patients with chronic, low back pain: 24-month results of a prospective multicenter study," Pain Medicine 15(3): Mar. 2014, pp. 347-354.
Abejon et al., "Electric parameters optimization in spinal cord stimulation. Study in conventional nonrechargeable systems" Neuromodulation 13(4): Mar. 2010, pp. 281-287.
Tiede et al., "Novel Spinal Cord Stimulation Parameters in Patients with Predominant Back Pain," Neuromodulation 16(4): Jan. 2013, pp. 370-375.
Van Buyten et al., "High-frequency spinal cord stimulation for the treatment of chronic back pain patients: results of a prospective multicenter European clinical study," Neuromodulation 16(1): Oct. 2012, 7 pp.
Perruchoud et al., "Analgesic efficacy of high-frequency spinal cord stimulation: a randomized double-blind placebo-controlled study," Neuromodulation 16(4): Feb. 2013, pp. 363-369.
Van Havenbergh et al., "Spinal Cord Stimulation for the Treatment of Chronic Back Pain Patients: 500-Hz vs. 1000-Hz Burst Stimulation," Neuromodulation 18(1): Jan. 2015, pp. 9-12.
Kapural et al., "Novel 10-kHz High-frequency Therapy (HF10 Therapy) Is Superior to Traditional Low-frequency Spinal Cord Stimulation for the Treatment of Chronic Back and Leg Pain: The SENZA-RCT Randomized Controlled Trial," Anesthesiology 123(4): Oct. 2015, pp. 851-860.
Hakkinen et at., "Changes in the total Oswestry Index and its ten items in females and males pre- and post-surgery for lumbar disc herniation: a 1-year follow-up," Eur Spine J. 16(3): Mar. 2007, pp. 347-352.
Fairbank et al., "The Oswestry Disability Index," Spine 25(22): Nov. 2000, pp. 2940-2953.
Hurst et al., "Assessing the clinical significance of change scores recorded on subjective outcome measures," Journal of Manipulative Physiological Therapeutics (IMPT) 27(1): Jan. 2004, pp. 26-35.

* cited by examiner

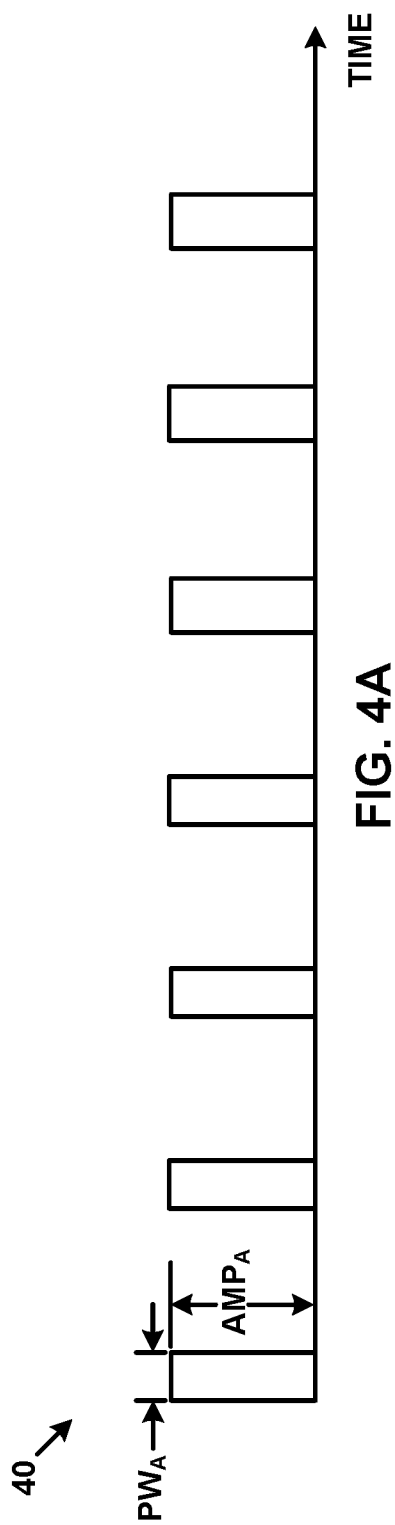
FIG. 4A
FIG. 4B

CATHODE-MINIMIZED STIMULATION PROGRAMMING

This application is a U.S. national stage entry under 35 U.S.C. § 371 of International Application No. PCT/US2017/047977, filed on Aug. 22, 2017, which claimed the benefit of U.S. Provisional Application No. 62/404,018, filed on Oct. 4, 2016. The entire contents of each of these applications is incorporated herein by reference.

TECHNICAL FIELD

The present disclosure relates to electrical stimulation therapy.

BACKGROUND

Medical devices may be external or implanted, and may be used to deliver electrical stimulation therapy to various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient.

SUMMARY

The present disclosure is directed to medical devices, systems, and techniques for programming a stimulator device to deliver stimulation therapy at high-density parameter settings using a cathode-minimized electrode configuration that has been determined to induce paresthesia over a patient pain pattern at low-density parameter settings.

BRIEF DESCRIPTION OF DRAWINGS

FIG. 4A illustrates an example low-density electrical stimulation signal.

FIG. 4B illustrates an example high-density electrical stimulation signal.

DETAILED DESCRIPTION

Figure 1:
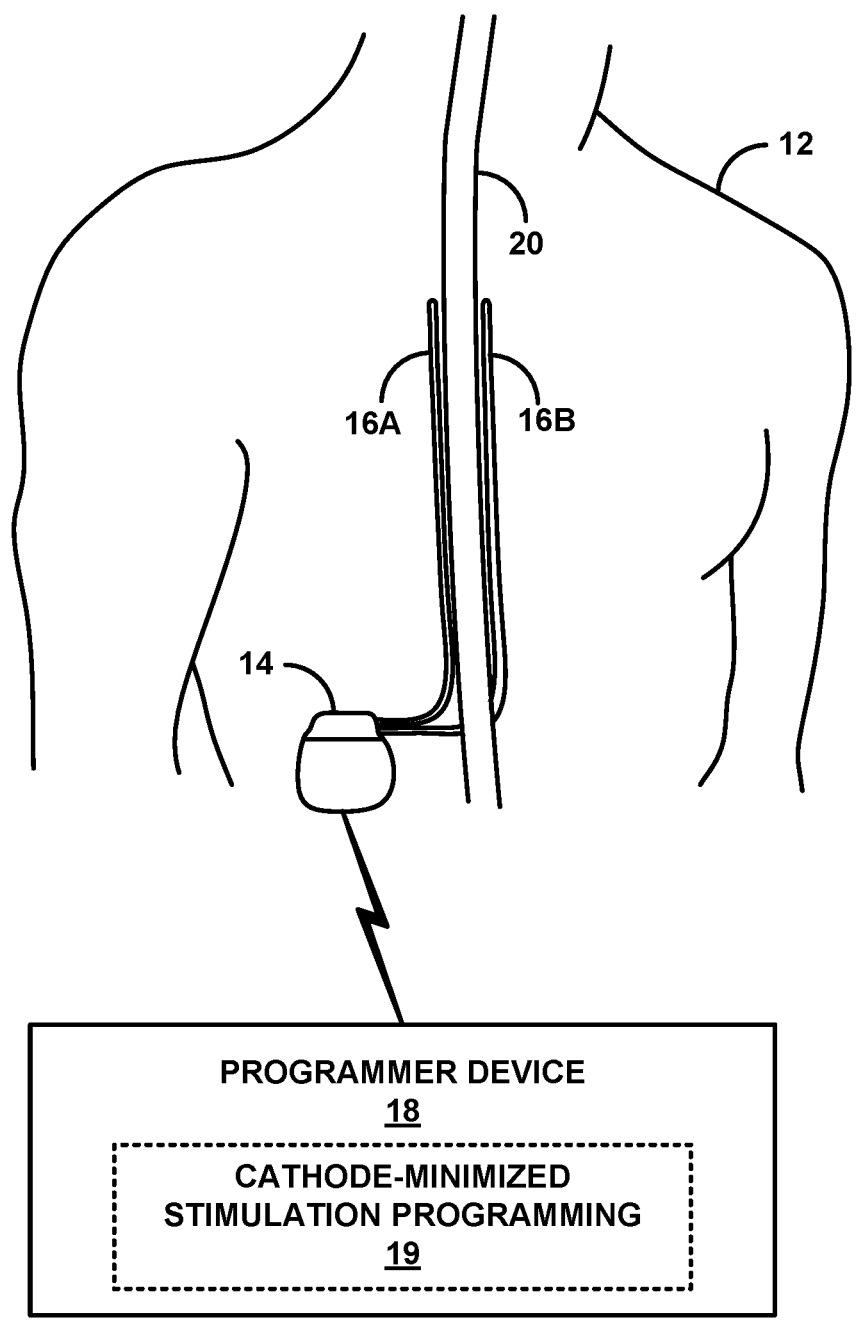
FIG. 1 illustrates an example medical device system in accordance with the disclosure.

In an aspect, this disclosure describes example medical devices, systems, and techniques for delivering electrical stimulation therapy to treat one or more patient conditions, the electrical stimulation therapy providing a relatively high amount of electrical stimulation per unit of time (referred to herein as a "high-dose" or "high density") and a stimulation intensity less than a perception or paresthesia threshold intensity level of the patient. The dose of electrical stimulation, which may be either "high-dose" or "low-dose" (i.e., a relatively low amount of electrical stimulation per unit of time) may be a function of a frequency and pulse width of the pulses. The perception threshold intensity level may be the lowest determined stimulation intensity level at which a patient perception of the electrical stimulation occurs, and the paresthesia threshold intensity level may be the lowest determined stimulation intensity level at which the electrical stimulation causes paresthesia, for example, within a predetermined time range (e.g., 30 seconds) of the patient receiving the electrical stimulation.

The high-dose of electrical stimulation therapy described herein delivers a relatively high amount of energy to tissue of the patient per unit of time. For example, the high-dose of electrical stimulation therapy may have a charge delivery of about 100 microCoulombs to about 2,000 microCoulombs per second. The low-dose of electrical stimulation therapy described herein delivers a relatively low amount of energy to tissue of the patient per unit of time. For example, the low-dose of electrical stimulation therapy may have a charge delivery of less than 100 microCoulombs per second. The sufficiency of electrical stimulation in producing a desired therapeutic effect may be based on the amount of charge delivered to the tissue of the patient per unit of time. In the case of electrical stimulation pulses, the amount of charge delivered to the tissue of the patient per unit of time may be calculated by multiplying the electrical current delivered during an electrical pulse by the pulse width, which yields the amount of electrical charge delivered during a single pulse, and multiplying the amount of electrical charge delivered to the patient for one pulse by the frequency of the electrical stimulation signal. Several examples of such a calculation are provided below.

The high energy dose electrical stimulation described herein may be provided by an electrical stimulation signal having a relatively high duty cycle. The low energy dose electrical stimulation described herein may be provided by an electrical stimulation signal having a relatively low duty cycle. The duty cycle may be, for example, the percentage of active electrical stimulation per unit of time (e.g., one second), and may, for example, be a product of a frequency of the pulses and a pulse width of the pulses. Thus, the duty cycle may, in some examples, by defined by a plurality of pulses per unit of time, rather than a single pulse. However, other waveforms may be used in other examples.

In some examples, a medical device is configured to generate and deliver, via one or more electrodes, an electrical stimulation signal having a high duty cycle and a frequency less than or equal to about 1400 Hertz (Hz), such as less than or equal to about 1000 Hz. The frequency may, for example, be in a range of about 1 Hz to about 1400 Hz, such as about 1000 Hz. The pulses may each have a relatively low amplitude (e.g., about 1 milliamp (mA) to about 25 mA, such as about 1 mA to about 5 mA), which can be the same or may vary between the pulses. In some examples, the duty cycle may be greater than 2% such as in a range of about 2% to about 50%, or about 20% to about 50%, or about 10% to about 40%, or about 20% to about 30%. Thus, in some examples, the frequency and pulse width of the pulses may be selected such that the electrical stimulation may have a duty cycle in a range of about 2% to about 50%, where the frequency is selected to be in a range of about 1 Hz to about 1400 Hz (e.g., less than or equal to about 1000 Hz) and the pulse width is selected to be in a range of about 0.1 ms to about 5 ms (e.g., about 0.1 ms to about 1 ms). In some examples, the amplitude of the pulses may be selected to provide therapeutic efficacy and so that the intensity of the delivered electrical stimulation is less than or equal to one or both of a paresthesia threshold or perception threshold of the patient.

Due at least in part to a relatively high number of pulses per unit of time and the selected pulse width, the dose (e.g., charge per second delivered) of the electrical stimulation signal may be high enough to elicit a therapeutic response from the patient, even though each individual pulse may have a relatively low amplitude. The relatively low amplitude of the pulses may also help keep the stimulation intensity level less than a perception or paresthesia threshold intensity level for the patient. In some examples, the plurality of pulses may have a duty cycle in a range of about 2% to about 50% and a frequency less than or equal to about 1000 Hz, and each of the pulses may have a pulse width in a range of about 0.1 ms to about 5 ms, such as about 0.1 ms to about 1 ms, or about 500 μs to about 1 ms. For example, the plurality of pulses may have a duty cycle in a range of about 9% to about 50% and a frequency less equal to about 1000 Hz, and each of the pulses may have a pulse width less than or equal to about 0.5 ms.

In some examples in which the high duty cycle, relatively low stimulation intensity electrical stimulation is delivered to a tissue site in a patient proximate to the spinal cord, the electrical stimulation may modulate nerve fibers and produce pain relief via mechanisms that do not rely on the activation of dorsal column fibers. Although the electrical stimulation may or may not also activate dorsal column fibers, the electrical stimulation may not rely on activation of dorsal column fibers, which may cause paresthesia, to provide therapeutic efficacy for pain or another patient condition. For example, the high duty cycle electrical stimulation may block endogenous action potentials in A-beta fibers at their branch points. A-beta fibers may be involved in some forms of chronic pain modulation, and the high duty cycle electrical stimulation may prevent A-fiber information from reaching the dorsal horn. Activation of dorsal column axons may cause paresthesia. Thus, the pain relief from the high duty cycle electrical stimulation described herein using relatively low amplitude pulses may be substantially paresthesia-free in some examples and with some patients. The paresthesia-free electrical stimulation may be referred to as subliminal stimulation in some examples.

In some cases, the high duty cycle electrical stimulation described herein may modulate dural fibers, which may also be responsible for some aspects of pain (e.g., back pain) without causing activation of dorsal column fibers.

The mechanisms by which the high duty cycle, relatively low stimulation intensity electrical stimulation described herein may cause pain relief may include inhibition of spinal neurons, modulation of the activity of the central nervous system (CNS) and/or brainstem, or descending inhibition (e.g., suppression of pain messages to the brain).

The high duty cycle electrical stimulation techniques described herein may activate neurons in a different way than burst electrical stimulation techniques. In contrast to burst electrical stimulation techniques, the high duty cycle electrical stimulation described herein may provide better targeting of target tissue sites. For a given electrical stimulation dose (e.g., energy per second), burst electrical stimulation techniques may result in activation of more neural tissue (e.g., a larger volume of tissue) than the electrical stimulation described herein, which provides electrical stimulation with a higher frequency to achieve a dose sufficient to elicit a therapeutic response from a patient.

For example, the high duty cycle electrical stimulation described herein may deliver pulses having higher amplitudes, shorter pulse widths, or both higher amplitudes and shorter pulse widths than the burst electrical stimulation techniques. Compared to burst electrical stimulation techniques, the higher duty cycle described herein may allow for a larger therapeutic window for the amplitude of electrical stimulation (e.g., a range of values of the stimulation signal amplitude that provides efficacious electrical stimulation therapy), which may result in more freedom to titrate the amplitude of the pulses. The larger therapeutic window may help a clinician tailor the electrical stimulation to a particular patient to allow for different neural mechanisms to be activated in order to elicit a therapeutic response from the patient, e.g., while maintaining the intensity of the electrical stimulation below a threshold stimulation intensity level. In addition, the larger therapeutic window for the amplitude may provide a clinician with more freedom to select therapy parameter values that balance power efficiency (power consumed by the IMD when generating the electrical stimulation) with the therapeutic effect.

In some examples, a therapeutic window is defined as the values of an electrical stimulation parameter between an efficacy threshold, which may be the lowest electrical stimulation parameter value (or highest, depending on the parameter) at which efficacious effects of the electrical stimulation were first observed, and an adverse-effects threshold, which may be the lowest electrical stimulation parameter value (or highest, depending on the parameter) at which adverse effects of the electrical stimulation were first observed.

The high duty cycle electrical stimulation described herein may also provide better targeting of target tissue sites compared to high frequency electrical stimulation techniques, in which a plurality of pulses are delivered at frequencies greater than or equal to 1.5 kilohertz (kHz). For a given dose, the high frequency electrical stimulation techniques may result in activation of more neural tissue than the high duty cycle electrical stimulation described herein, which provides electrical stimulation with wider pulse widths, but at lower frequencies than the high frequency electrical stimulation techniques to achieve a dose sufficient to elicit a therapeutic response from a patient. Compared to high frequency electrical stimulation techniques, the lower frequency of the high duty cycle electrical stimulation described herein may allow for a larger therapeutic window for the amplitude of electrical stimulation. As discussed above, a larger therapeutic window may help a clinician tailor the electrical stimulation to a particular patient and may provide the clinician with more freedom to select therapy parameter values that balance power efficiency with the therapeutic effect.

The high duty cycle electrical stimulation as discussed however may prematurely deplete or accelerate the depletion of the battery of implantable or implanted stimulation devices. Thus, a cathode-minimized programming algorithm is contemplated to increase the battery lifetime of implantable stimulation devices configured to deliver high-dose or high duty cycle or high-density electrical stimulation therapy. In examples, "low dose" or "low duty" cycle electrical stimulation may initially be leveraged to demonstrate paresthesia coverage over a patient pain pattern. In the context of the present disclosure, certain values for pulse width and pulse rate that when considered together may constitute low-density, or low-dose or low duty cycle therapy programming, and certain values for pulse width and pulse rate that when considered together may constitute high-density, or high-dose, or high duty cycle therapy programming, where a threshold value calculated from or using pulse width and pulse rate may distinguish high-density therapy programming from low-density therapy programming. Then, a process of testing paresthesia coverage over the patient pain pattern may be performed using a number of different electrode configurations, with the goal of identifying the electrode configuration that exhibits the least number of cathodes while still demonstrating paresthesia (increasing stimulation amplitude past perception) coverage over the patient pain pattern. Minimizing the number of cathodes directly translates into more efficient use of battery power because a cathode typically draws about 4× as much power from a battery as compared to an anode.

Once the electrode configuration that exhibits the least number of cathodes while still demonstrating paresthesia coverage over the patient pain pattern is determined, high-dose or high duty cycle electrical stimulation may be programmed, and an adjustment to stimulation amplitude may be made by increasing stimulation amplitude to the lowest perception threshold (not increasing stimulation amplitude past perception) and then decreasing the stimulation amplitude by a predetermined value (e.g., 0.3 V), which corresponds to a patient "comfort" amplitude that would be used to deliver stimulation therapy to the patient. In general, such an algorithm may correspond to programming a stimulator device to deliver stimulation therapy at high-density parameter settings using a cathode-minimized electrode configuration determined to induce paresthesia over a patient pain pattern at low-density parameter settings. Although not so limited, and appreciation of the various features or aspects of the present disclosure may be gained from the following discussion in connection with the drawings.

For example, FIG. 1 is a conceptual diagram illustrating example system 10 that includes an implantable medical device (IMD) 14 configured to deliver electrical stimulation therapy to patient 12. In the example shown in FIG. 1, IMD 14 is configured to deliver SCS therapy. Although the techniques described in this disclosure are generally applicable to a variety of medical devices including external and implantable medical devices (IMDs), application of such techniques to IMDs and, more particularly, implantable electrical stimulators (e.g., neurostimulator) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 10 includes an IMD 14, leads 16A, 16B, and external programmer 18 shown in conjunction with a patient 12, who is ordinarily a human patient. In the example of FIG. 1, IMD 14 is an implantable electrical stimulator that is configured to generate and deliver electrical stimulation therapy to patient 12 via electrodes of leads 16A, 16B, e.g., for relief of chronic pain or other symptoms. IMD 14 may be a chronic electrical stimulator that remains implanted within patient 12 for weeks, months, or even years. In other examples, IMD 14 may be a temporary, or trial, stimulator used to screen or evaluate the efficacy of high-dose or high duty cycle electrical stimulation for chronic therapy.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone, polyurethane, or a liquid crystal polymer, and surgically implanted at a site in patient 12 near the pelvis, abdomen, or buttocks. In other examples, IMD 14 may be implanted within other suitable sites within patient 12, which may depend, for example, on the target site within patient 12 for the delivery of electrical stimulation therapy. The outer housing of IMD 14 may be configured to provide a hermetic seal for components, such as rechargeable power source 18. In addition, in some examples, the outer housing of IMD 14 may be selected of a material that facilitates receiving energy to charge rechargeable power source 38 (see FIG. 2).

Electrical stimulation energy, which may be constant current or constant voltage based pulses, for example, is delivered from IMD 14 to one or more target tissue sites of patient 12 via one or more electrodes (see FIG. 2) of implantable leads 16A and 16B (collectively "leads 16"). In the example of FIG. 1, leads 16 carry electrodes that are placed adjacent to the target tissue of spinal cord 20. One or more of the electrodes may be disposed at a distal tip of a lead 16 and/or at other positions at intermediate points along the lead. Leads 16 may be implanted and coupled to IMD 14. The electrodes may transfer electrical stimulation generated by an electrical stimulation generator in IMD 14 to tissue of patient 12. Although leads 16 may each be a single lead, lead 16 may include a lead extension or other segments that may aid in implantation or positioning of lead 16. In some other examples, IMD 14 may be a leadless stimulator with one or more arrays of electrodes arranged on a housing of the stimulator rather than leads that extend from the housing. In addition, in some other examples, system 10 may include one lead or more than two leads, each coupled to IMD 14 and directed to similar or different target tissue sites.

The electrodes of leads 16 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. Ring electrodes arranged at different axial positions at the distal ends of lead 16 will be described for purposes of illustration.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

The therapy parameters for a therapy program (also referred to as a set of electrical stimulation parameter values or settings) that controls delivery of stimulation therapy by IMD 14 through the electrodes of leads 16 may include information identifying which electrodes have been selected for delivery of stimulation according to a stimulation program, the polarities (anode or cathode) of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as rate or the like in the case IMD 14 is also configured for drug delivery.

Although FIG. 1 is directed to SCS therapy, e.g., used to treat pain, in other examples system 10 may be configured to treat any other condition that may benefit from electrical stimulation therapy. For example, system 10 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 12.

In some examples, lead 16 may include one or more sensors configured to allow IMD 14 to monitor one or more parameters of patient 12. The one or more sensors may be provided in addition to, or in place of, therapy delivery by lead 16.

IMD 14 is configured to deliver low-dose and high-dose (also referred to as low/high duty cycle or low/high density) electrical stimulation therapy to patient 12 via selected combinations of electrodes carried by one or both of leads 16, alone or in combination with an electrode carried by or defined by an outer housing of IMD 14. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 20, such as within an intrathecal space or epidural space of spinal cord 20, or, in some examples, adjacent nerves that branch off of spinal cord 20. Leads 16 may be introduced into spinal cord 18 in via any suitable region, such as the thoracic, cervical or lumbar regions. Stimulation of spinal cord 18 may, for example, prevent pain signals from traveling through spinal cord 20 and to the brain of patient 12. Patient 12 may perceive the interruption of pain signals as a reduction in pain and, therefore, efficacious therapy results.

IMD 14 generates and delivers electrical stimulation therapy to a target stimulation site within patient 12 via the electrodes of leads 16 to patient 12 according to one or more therapy programs. A therapy program defines values for one or more parameters that define an aspect of the therapy delivered by IMD 14 according to that program. For example, a therapy program that controls delivery of stimulation by IMD 14 in the form of pulses may define values for voltage or current pulse amplitude, pulse width, and pulse rate for stimulation pulses delivered by IMD 14 according to that program. In the context of the present disclosure, certain values for pulse width and pulse rate that when considered together may constitute low-density, or low-dose or low duty cycle therapy programming, and certain values for pulse width and pulse rate that when considered together may constitute high-density, or high-dose, or high duty cycle therapy programming, where a threshold value calculated from or using pulse width and pulse rate may distinguish high-density therapy programming from low-density therapy programming.

Moreover, in some examples, IMD 14 delivers electrical stimulation therapy to patient 12 according to multiple therapy programs, which may be stored as a therapy program group. For example, as described below, in some examples, IMD 14 may deliver different pulses of a high duty cycle electrical stimulation signal via respective electrode combinations, and each of the electrode combinations may be associated with a respective therapy program. The therapy programs may be stored as a group, such that when IMD 14 generates and delivers electrical stimulation therapy via a selected group, IMD 14 delivers high duty cycle electrical stimulation signal via two or more therapy programs. Similarly, IMD 14 may deliver different pulses of a low duty cycle electrical stimulation signal via respective electrode combinations, and each of the electrode combinations may be associated with a respective therapy program. The therapy programs may be stored as a group, such that when IMD 14 generates and delivers electrical stimulation therapy via a selected group, IMD 14 delivers low duty cycle electrical stimulation signal via two or more therapy programs. Measuring group impedance and/or current draw in the context of these example corresponds to measuring impedance and/or current draw for the group or configuration of electrodes for a particular therapy program stored as a group. For example, with reference to FIG. 5, the leftmost program 52 may be referred to as a group and measuring group impedance and/or current draw in the context of this example may correspond to measuring impedance and/or current draw for the group or configuration of electrodes (+−++) shown programmed for lead 24. The current draw for the group or configuration of electrodes (+−−+) in this example may be reduced or modified by adjustment of simulation amplitude (e.g., reducing current draw by decreasing stimulation amplitude form 1.5 V to 1.3 V).

IMD 14 is configured to deliver a recharge signal (e.g., one or more recharge pulses or other waveforms), which may help balance a charge accumulation that may occur within tissue proximate the electrodes used to deliver the electrical stimulation. The recharge signal may also be referred to as a "recovery signal" or a "charge balancing signal" and may have a polarity opposite to that of the electrical stimulation signal generated and delivered by IMD 14. While recharge pulses are primarily referred to herein, in other examples, a recharge signal can have any suitable waveform.

Figure 5:
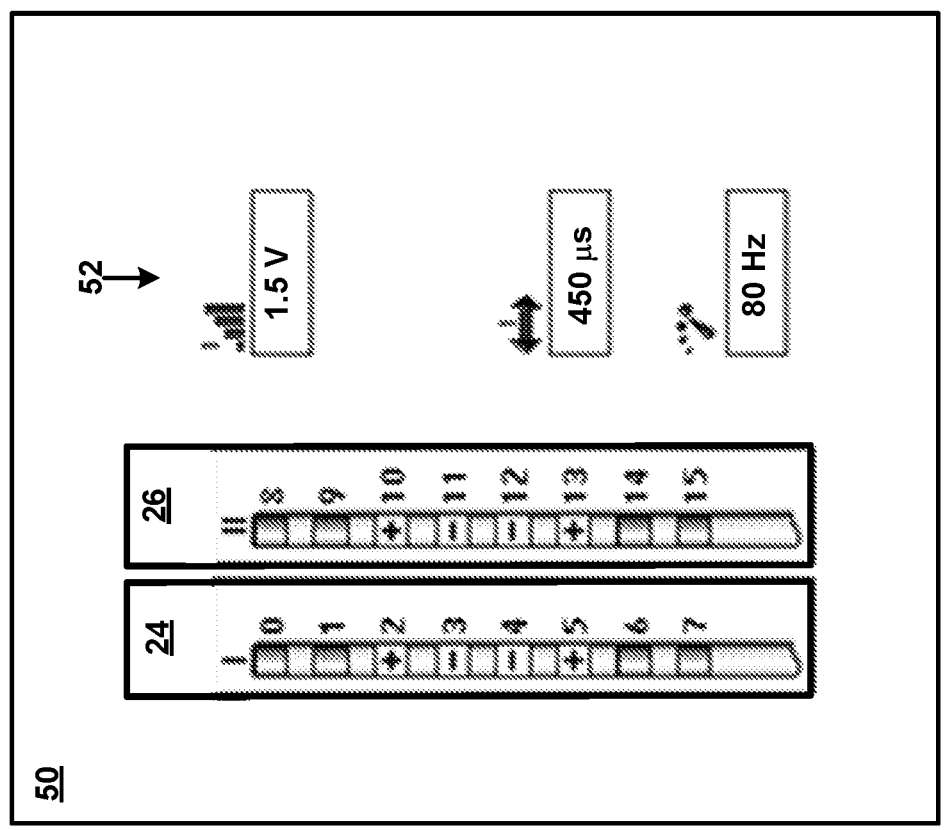
FIG. 5 illustrates an example user interface for cathode-minimized stimulation programming.
Figure 6:
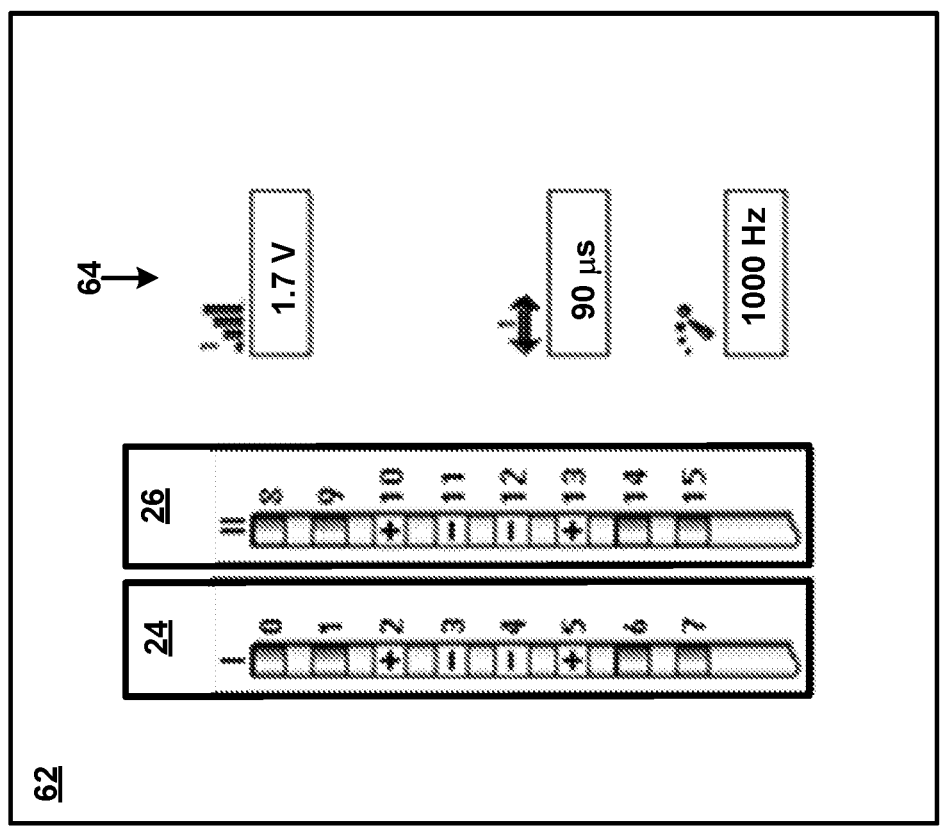
FIG. 6 illustrates another example user interface for cathode-minimized stimulation programming.

In some examples, IMD 14 may deliver a recharge signal after delivery of multiple pulses of a high duty electrical stimulation signal, which may be defined by one therapy program or by multiple therapy programs (see e.g., FIG. 6). Thus, rather than charge balancing on a pulse-by-pulse basis (e.g., delivering one recharge pulse after each electrical stimulation pulse), in some examples, IMD 14 delivers one or more recharge pulses after delivery of two or more electrical stimulation pulses. In some examples, IMD 14 delivers a high duty or low duty electrical stimulation signal to patient 12 according to multiple therapy programs by at least interleaving pulses of two or more therapy programs, the pulses having a first polarity (see e.g., FIG. 5). In some of these examples, IMD 14 may wait to deliver one or more recharge pulses until after one or more pulses of each of the therapy programs are delivered, each recharge pulse having a second polarity opposite to the first polarity. Thus, in some examples, IMD 14 may not deliver any recharge signals between therapy programs, but, rather, may withhold the delivery of one or more recharge signals until after IMD 14 delivers a plurality of pulses according to two or more therapy programs.

In some examples, IMD 14 is configured to generate and deliver high duty cycle electrical stimulation therapy to patient 12 via two or more electrodes, e.g., of leads 16 and/or a housing of IMD 14. In some examples, the high duty cycle electrical stimulation signal may have a duty cycle in a range of about 9% to about 50%, a frequency in a range of about 1 Hz to about 1400 Hz (e.g., less than about 1000 Hz in some examples), and a pulse width less than or equal to about 5 ms, such as about 0.1 ms to about 5 ms, or about 0.1 ms to about 1 ms. The amplitude and pulse width of the electrical stimulation signal are selected such that a stimulation intensity level of the electrical stimulation signal is less than a perception or paresthesia threshold intensity level for patient 12. For example, the amplitude may be selected to be in a range of about 1 mA to about 25 mA, such as in a range of about 1 mA to about 5 mA. In terms of voltage, the amplitude may be selected to be in a range of about 0.15 V to about 15.0 V, such as in a range of about 1.05 V to about 10.5 V.

In some examples, IMD 14 delivers the pulses of the high duty cycle electrical stimulation signal via different electrode combinations. For example, IMD 14 may alternate delivery of pulses between two different electrode combinations, or may otherwise interleave the pulses using two or more electrode combinations in any suitable order. Regardless of the number of electrode combinations with which IMD 14 delivers the pulses, however, the combination of pulses delivered over time define an electrical stimulation signal that may have a duty cycle in a range of about 9% to about 50% and a frequency in a range of about 1 Hz to about 1400 Hz.

A user, such as a clinician or patient 12, may interact with a user interface of an external programmer 18 to program IMD 14. Programming of IMD 14 may refer generally to the generation and transfer of commands, programs, or other information to control the operation of IMD 14. In this manner, IMD 14 may receive the transferred commands and programs from programmer 18 to control stimulation therapy. For example, external programmer 18 may transmit therapy programs, stimulation parameter adjustments, therapy program selections, therapy program group selections, user input, or other information to control the operation of IMD 14, e.g., by wireless telemetry or wired connection. In the context of the present disclosure, external programmer 18 may transmit cathode-minimized stimulation therapy programming 19, therapy programs, stimulation parameter adjustments, therapy program selections, therapy program group selections, user input, or other information to control the operation of IMD 14 to deliver stimulation therapy using both low-density stimulation parameter settings and high-density stimulation parameter settings using a cathode-minimize electrode configuration or stimulation vector.

In some cases, external programmer 18 may be characterized as a physician or clinician programmer if it is primarily intended for use by a physician or clinician. In other cases, external programmer 18 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy. In general, a physician or clinician programmer may support selection and generation of programs by a clinician for use by IMD 14, whereas a patient programmer may support adjustment and selection of such programs by a patient during ordinary use. In other examples, external programmer 18 may be included, or part of, an external charging device that recharges a power source of IMD 14. In this manner, a user may program and charge IMD 14 using one device, or multiple devices.

As described herein, cathode-minimized stimulation therapy programming 19 and information may be transmitted between external programmer 18 and IMD 14. Therefore, IMD 14 and programmer 18 may communicate via wireless communication using any techniques known in the art. Examples of communication techniques may include, for example, radiofrequency (RF) telemetry and inductive coupling, but other techniques are also contemplated. In some examples, programmer 18 may include a communication head that may be placed proximate to the patient's body near the IMD 14 implant site in order to improve the quality or security of communication between IMD 14 and programmer 18. Communication between programmer 18 and IMD 14 may occur during power transmission or separate from power transmission.

Although IMD 14 is generally described herein, techniques of this disclosure may also be applicable to external or partially external medical device in other examples. For example, IMD 14 may instead be configured as an external medical device coupled to one or more percutaneous medical leads. The external medical device may be a chronic, temporary, or trial electrical stimulator. In addition, an external electrical stimulator may be used in addition to one or more IMDs 14 to deliver electrical stimulation described herein.

Figure 2:
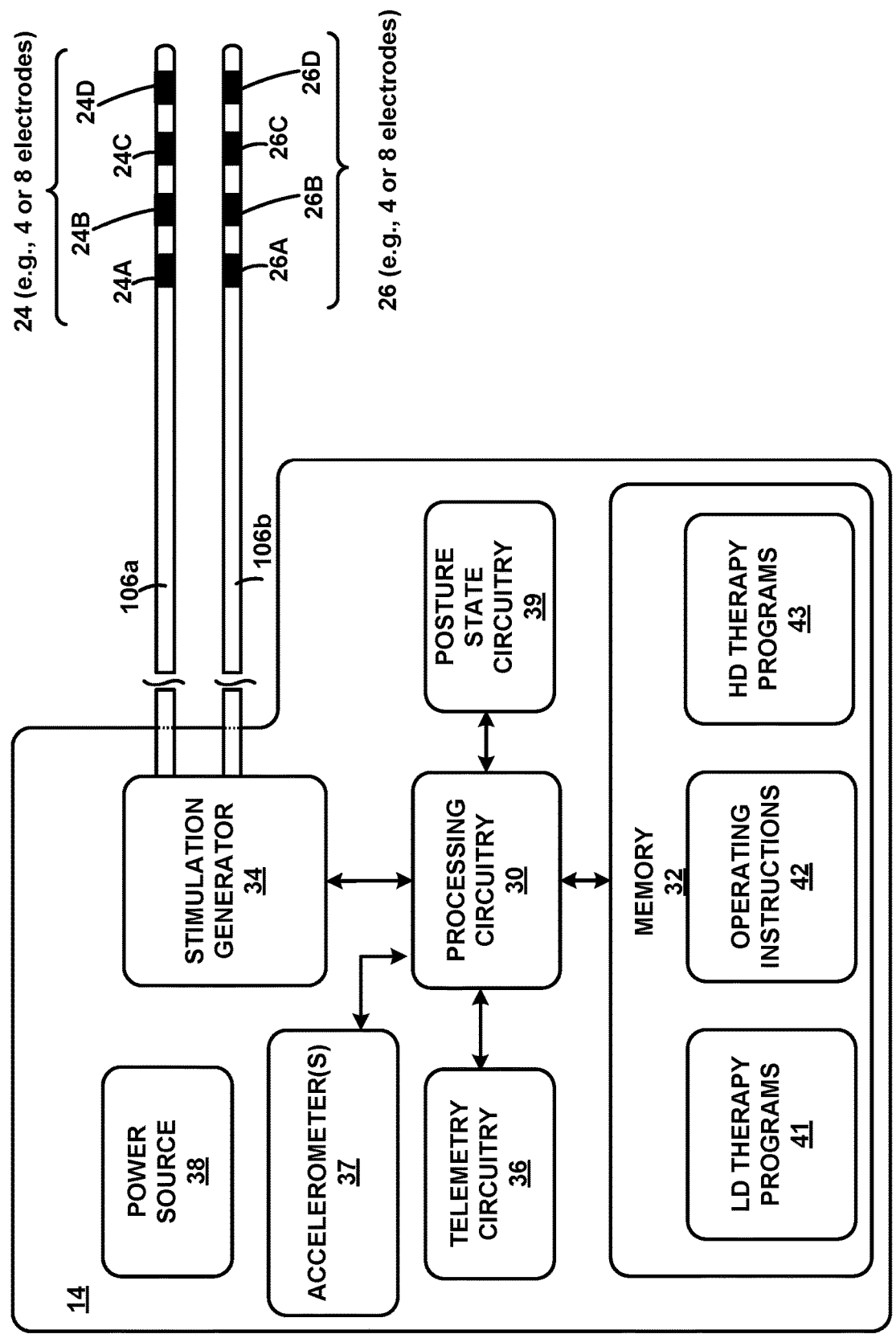
FIG. 2 is a block diagram that illustrates an example configuration of the stimulator device of the system of FIG. 1.

FIG. 2 is a functional block diagram illustrating various components of an example IMD 14. In the example shown in FIG. 2, IMD 14 includes processing circuitry 30, memory 32, stimulation generator 34, telemetry circuitry 36, one or more accelerometers 37 (e.g., a three-axis accelerometer), power source 38 and posture state circuitry 39. In practice, processing circuitry 30 may determine a current posture state of patient 12 based on output signals of the one or more accelerometers 37. For example, by comparing the output signals to threshold values a determination may be made as to whether the current posture state of patient 12 is upright, sitting and various types of supine (front, sides, back). Additionally, or alternatively, processing circuitry 30 may determine whether patient 12 is moving or in motion, and to what degree, based on output signals of the one or more accelerometers 37. In other examples, IMD 14 may include a greater or fewer number of components. For example, IMD 14 may also include sensing circuitry configured to sense one or more patient parameters, an inductive coil to receive power from an external charging device, and recharge circuitry that manages recharging of power source 38.

Processing circuitry 30 is operably connected to and configured to access information from memory 32 and to control stimulation generator 34 and telemetry circuitry 36. Components described as processing circuitry 30 and other processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. In general, IMD 14 may comprise any suitable arrangement of hardware, alone or in combination with software and/or firmware, to perform the various techniques described herein attributed to IMD 14 and processing circuitry 30. In various examples, IMD 14 may include one or component of processing circuitry 30, such as one or more DSPs, ASICs, FPGAs, programmable logic circuitry, or the like, either alone or in any suitable combination.

Memory 32 may store low-density therapy programs 41 and high-density therapy programs 43 (or other instructions that specify therapy parameter values and/or cathode-minimized electrode configurations for therapy provided by stimulation generator 34 and IMD 14), operating instructions 42 for execution by processing circuitry 30, and any other information regarding therapy of patient 12. In some examples, memory 32 may also store instructions for communication between IMD 14 and programmer 18, or any other instructions required to perform tasks attributed to IMD 14. Memory 32 may include separate memories for storing therapy programs, operating instructions, and any other data that may benefit from separate physical memory modules.

Memory 32 may comprise any suitable non-transitory memory, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Although, processing circuitry 30, stimulation generator 34, telemetry circuitry 36, and posture state circuitry 39 are described as separate modules, in some examples, processing circuitry 30, stimulation generator 34, telemetry circuitry 36, and posture state circuitry 39 may be functionally integrated. In some examples, processing circuitry 30, stimulation generator 34, telemetry circuitry 36, may correspond to individual hardware units, such as ASICs, DSPs, FPGAs, or other hardware units.

Stimulation generator 34 forms a therapy delivery module of IMD 14. Processing circuitry 30 controls stimulation generator 34 to generate and deliver electrical stimulation via electrode combinations formed by a selected subset of electrodes 24A-24D, 26A-26D (collectively, "electrodes 24, 26") of leads 16, where leads 16 may exhibit more electrodes (e.g., 8 electrodes apiece) depending on implementation-specific details. Stimulation generator 34 may deliver electrical stimulation therapy via electrodes on one or more of leads 16, e.g., as stimulation pulses. Stimulation generator 34 may include stimulation generation circuitry to generate stimulation pulses and, in some examples, switching circuitry to switch the stimulation across different electrode combinations, e.g., in response to control by processing circuitry 30. In other examples, stimulation generator 34 may include multiple current sources to drive more than one electrode combination at one time.

In some examples, processing circuitry 30 controls stimulation generator 34 by accessing memory 32 to selectively access and load at least one of the therapy programs 41, 43 to stimulation generator 34. The stimulation parameter values of the stored therapy programs 41, 43 may include, for example, a voltage amplitude, a current amplitude, a pulse frequency, a pulse width, a duty cycle, and a subset of electrodes 24, 26 of leads 16 for delivering the electrical stimulation signal. An electrode configuration may include the one or more electrodes 24, 26 with which stimulation generator 34 delivers the electrical stimulation to tissue of a patient, and the associated electrode polarities (anode/cathode).

In some examples, IMD 14 may deliver a high duty cycle electrical stimulation signal to a target tissue site within patient 12 via one electrode combination, such that all pulses are delivered via the same electrode combination. In some examples, IMD 14 may deliver a high duty cycle electrical stimulation signal to a target tissue site within patient 12 via one electrode combination, such that all pulses are delivered via the same electrode combination. In other examples, IMD 14 may deliver a high duty cycle electrical stimulation signal to a target tissue site within patient 12 via two or more electrode combinations, such that IMD 14 delivers at least two different pulses of a high duty cycle electrical stimulation signal via respective electrode combinations In other examples, IMD 14 may deliver a low duty cycle electrical stimulation signal to a target tissue site within patient 12 via one electrode combination, such that all pulses are delivered via the same electrode combination. In other examples, IMD 14 may deliver a low duty cycle electrical stimulation signal to a target tissue site within patient 12 via two or more electrode combinations, such that IMD 14 delivers at least two different pulses of a low duty cycle electrical stimulation signal via respective electrode combinations. The delivery of different pulses via respective electrode combinations may help target the electrical stimulation to a target tissue site (e.g., in the case of pain relief, the target may be towards a midline of spinal cord 20, for example, near the T9-T10 vertebrae). The electrical stimulation delivered by each electrode combination, which may be referred to as a sub-signal, may be interleaved (e.g., delivered at different times) to define the high duty cycle or low duty cycle electrical stimulation signal. In some of these examples, each sub-signal is associated with a respective therapy program. Thus, processing circuitry 30 may control stimulation generator 34 to generate and deliver a high duty cycle electrical stimulation signal or a low duty cycle electrical stimulation signal by at least accessing memory 32 to selectively access and load multiple therapy programs 41, 43 to stimulation generator 34.

IMD 14 also includes components to receive power from programmer 18 or a separate charging device to recharge a battery of power source 38. Power source 38 may include one or more capacitors, batteries, or other energy storage devices. IMD 14 may thus also include an inductive coil and recharge circuitry (both not shown) configured to manage the recharging session for power source 38. Although inductive coupling may be used to recharge power source 38, other wireless energy transfer techniques may alternatively be used. Alternatively, power source 38 may not be rechargeable.

Processing circuitry 30 may also control the exchange of information with programmer 18 and/or an external programmer using telemetry circuitry 36. Telemetry circuitry 36 may be configured for wireless communication using RF protocols, inductive communication protocols, or any other suitable technique. To support the wireless communication, telemetry circuitry 36 may include appropriate electronic components, such as amplifiers, filters, mixers, encoders, decoders, and the like. Processing circuitry 30 may transmit operational information and receive therapy programs or therapy parameter adjustments via telemetry circuitry 36. Also, in some examples, IMD 14 may communicate with other implanted devices, such as stimulators, control devices, or sensors, via telemetry circuitry 36.

Figure 3:
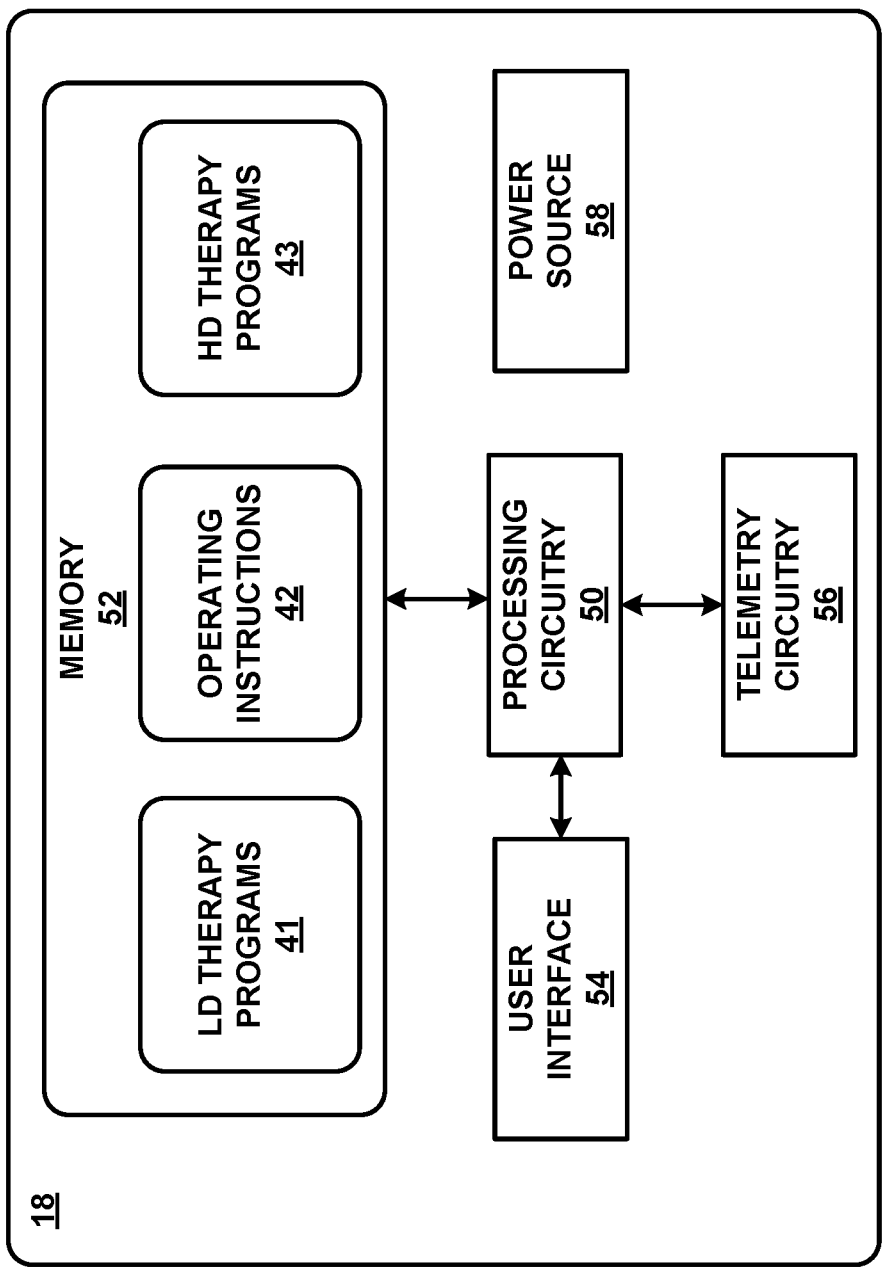
FIG. 3 illustrates an example configuration of the programmer device of the system of FIG. 1.

FIG. 3 is a block diagram of an example external programmer 18. While programmer 18 may generally be described as a hand-held device, programmer 18 may be a larger portable device or a more stationary device in some examples. In addition, in other examples, programmer 18 may be included as part of an external charging device or include the functionality of an external charging device. As illustrated in FIG. 3, programmer 18 may include a processing circuitry 50, memory 52, user interface 54, telemetry circuitry 56, and power source 58. Memory 52 may store instructions that, when executed by processing circuitry 50, cause processing circuitry 50 and external programmer 18 to provide the functionality ascribed to external programmer 18 throughout this disclosure.

Programmer 18 comprises any suitable arrangement of hardware, alone or in combination with software and/or firmware, to perform the techniques attributed to programmer 18, and processing circuitry 50, user interface 54, and telemetry circuitry 56 of programmer 18. In various examples, processing circuitry 50 may include one or more processors, such as one or more microprocessors, DSPs, ASICs, FPGAs, or any other equivalent integrated or discrete logic circuitry, as well as any combinations of such components. Programmer 18 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processing circuitry 50 and telemetry circuitry 56 are described as separate modules, in some examples, processing circuitry 50 and telemetry circuitry 56 are functionally integrated. In some examples, processing circuitry 50 and telemetry circuitry 56 correspond to individual hardware units, such as ASICs, DSPs, FPGAs, or other hardware units.

Memory 52 may store instructions that, when executed by processing circuitry 50, cause processing circuitry 50 and programmer 18 to provide the functionality ascribed to programmer 18 throughout this disclosure. In addition, in some examples, memory 52 may store low-density therapy programs 41 and high-density therapy programs 43, operating instructions 42, and any other information regarding therapy of patient 12 (or other instructions that specify therapy parameter values and/or cathode-minimized electrode configurations for therapy provided by stimulation generator 34 and IMD 14).

User interface 54 may include a button or keypad, lights, a speaker for voice commands, a display, such as a liquid crystal (LCD), light-emitting diode (LED), or organic light-emitting diode (OLED). In some examples the display may be a touch screen. User interface 54 may be configured to display any information related to the delivery of stimulation therapy, such as currently selected parameter values, intensity thresholds, or any other therapy information. User interface 54 may also receive user input via user interface 54. The input may be, for example, in the form of pressing a button on a keypad or selecting an icon from a touch screen. The input may request starting or stopping electrical stimulation, or requesting some other change to the delivery of electrical stimulation.

Telemetry circuitry 56 may support wireless communication between IMD 14 and programmer 18 under the control of processing circuitry 50. Telemetry circuitry 56 may also be configured to communicate with another computing device via wireless communication techniques, or direct communication through a wired connection. In some examples, telemetry circuitry 56 may be substantially similar to telemetry circuitry 36 of IMD 14 described herein, providing wireless communication via an RF or proximal inductive medium. In some examples, telemetry circuitry 56 may include an antenna, which may take on a variety of forms, such as an internal or external antenna.

Examples of local wireless communication techniques that may be employed to facilitate communication between programmer 18 and IMD 14 include RF communication according to the 802.11 or Bluetooth specification sets or other standard or proprietary telemetry protocols. In this manner, other external devices may be capable of communicating with programmer 18 without needing to establish a secure wireless connection.

FIG. 4A is a timing diagram of an example low-density electrical stimulation signal 40 that IMD 14 may generate and deliver to patient 12. Electrical stimulation signal 40 includes a plurality of pulses. Although seven pulses are shown in FIG. 4A, stimulation signal 40 may include any number of pulses, which may depend on the time period over which IMD 14 delivers stimulation signal 40 to patient 12. In this example, each pulse has an amplitude $AMP_A$ and a pulse width $PW_A$. In other examples, at least one pulse of signal 40 may have a different amplitude and/or pulse width than another pulse. However, in either example, electrical stimulation signal 40 has a duty cycle of about 2% to about 9% and a frequency in a range of about 1 Hz to about 1400 Hz or less (e.g., less than or equal to about 1000 Hz). In addition, in some examples, each pulse may have a pulse width in a range of about 0.1 ms to about 5 ms (e.g., less than or equal to about 1 ms, such as in a range of about 0.5 ms to about 1 ms).

The duty cycle of electrical stimulation signal 40, which may be the on-time of electrical stimulation signal 40 per unit of time (e.g., one second), can be characterized by a product of a frequency and a pulse width of pulses of the signal, sometimes referred to as pulse-density. For example, for stimulation signal 40 having a frequency of about 80 Hz and a pulse width of about 450 microseconds (µs) (0.00045 seconds), stimulation signal 40 may have a duty cycle of about 3.6%, calculated as follows:

$$\text{Duty Cycle} = 80 \text{ pulses} * 0.00045 \text{ sec} = 0.036 \text{ sec}$$
$$\text{therapy "on time"} = 3.6\%$$

Duty cycle may be used to distinguish a low-density or low-dose electrical stimulation signal from a high-density or high-dose electrical stimulation signal.

For example, FIG. 4B is a timing diagram of an example high-density electrical stimulation signal 60 that IMD 14 may generate and deliver to patient 12. Electrical stimulation signal 60 includes a plurality of pulses. Although seventeen pulses are shown in FIG. 4B, stimulation signal 60 may include any number of pulses, which may depend on the time period over which IMD 14 delivers stimulation signal 60 to patient 12. Each pulse has an amplitude $AMP_B$ and a pulse width $PW_B$. In some examples, each pulse of electrical stimulation signal 60 can have the same amplitude and pulse width. In other examples, at least one pulse of signal 60 may have a different amplitude and/or pulse width than another pulse. However, in either example, electrical stimulation signal 60 has a duty cycle of about 9% to about 50% and a frequency in a range of about 1 Hz to about 1400 Hz or less (e.g., less than or equal to about 1000 Hz). In addition, in some examples, each pulse may have a pulse width in a range of about 0.1 ms to about 5 ms (e.g., less than or equal to about 1 ms, such as in a range of about 0.5 ms to about 1 ms).

The duty cycle of electrical stimulation signal 60, which may be the on-time of electrical stimulation signal 60 per unit of time (e.g., one second), can be characterized by a product of a frequency and a pulse width of pulses of the signal. For example, for stimulation signal 60 having a frequency of about 1000 Hz and a pulse width of about 90 microseconds (µs) (0.00009 seconds), stimulation signal 60 may have a duty cycle of about 9%, calculated as follows:

Duty Cycle=1000 pulses*0.00009 sec=0.09 sec therapy "on time"=9.0%

As another example, for stimulation signal 60 having a frequency of about 500 Hz and a pulse width of about 500 µs, stimulation signal 60 may have a duty cycle of about 25%, calculated as follows:

Duty Cycle=500 pulses*0.0005 sec=0.25 sec therapy "on time"=25.0%

As mentioned, duty cycle may be used to distinguish a low-density or low-dose electrical stimulation signal from a high-density or high-dose electrical stimulation signal. For example, a threshold of 9% may be used to distinguish a low-density electrical stimulation signal from a high-density electrical stimulation signal. In this example, an electrical stimulation signal that has a duty cycle (calculated in a manner as described) less than 9% may be characterized as a low-density electrical stimulation signal, such as the signal illustrated in FIG. 4A. In contrast, an electrical stimulation signal that has a duty cycle (calculated in a manner as described) greater than or equal to 9% may be characterized as a high-density electrical stimulation signal, such as the signal illustrated in FIG. 4B. It is contemplated that the threshold may be defined as desired, and may be a function of the pain relief mechanism attributed to a particular signal. For example, a low-density electrical stimulation signal may engage endogenous opioid mechanisms or may more preferentially activate peripheral blood flow mechanisms, whereas a separate neural mechanism may be engaged by a high-density electrical stimulation signal. Regardless, it is contemplated that frequency and rate parameters of an electrical stimulation signal when taken or considered together in a manner as discussed throughout may be used to distinguish a low-density electrical stimulation signal from a high-density electrical stimulation signal.

In some examples, for a frequency of less than or equal to about 1000 Hz, the pulse width of pulses of signal can be selected such that stimulation signal 60 has a duty cycle of about 9% to about 50%. In addition, the amplitude of stimulation signal 60 can be selected such that the dose of electrical stimulation signal 60 (having the desired duty cycle) is sufficient to elicit a therapeutic response from patient 12 when IMD 14 delivers electrical stimulation signal 60 to a target tissue site in patient 12 (e.g., proximate spinal cord 20, a peripheral nerve, a muscle, or another suitable tissue site, which may be selected based on the patient condition being treated). For example, in examples in which pulses of the signal 60 are substantially similar (e.g., identical or nearly identical amplitudes and pulse widths), the dose of electrical stimulation signal 60 can be determined to be a product of the amplitude and pulse width of the pulses of the signal, which are the pulses delivered over a one second period of time. In some examples in which IMD 14 delivers stimulation signal 60 to patient 12 to spinal cord 20 to treat pain, stimulation signal 60 may have a duty cycle of about 9% to about 50%, a frequency in a range of about 1 Hz to about 1400 Hz, and pulses of the signal 60 may each have a pulse width in a range of about 0.1 ms to about 5 ms and an amplitude below a paresthesia threshold of patient 12.

Stimulation generator 34 of IMD 14 may generate and deliver high duty cycle electrical stimulation signal 60 using any suitable technique. In some examples, stimulation generator 34 may deliver each of the pulses of stimulation signal 60 with the same electrode combination. In some examples, stimulation generator 34 may deliver one or more recharge pulses (also referred to as a "recovery pulse" or a "charge balancing pulse") after a predetermined number of pulses are delivered, the predetermined number being greater than one. Thus, rather than charge balancing on a pulse-by-pulse basis (e.g., delivering one recharge pulse after each pulse), in some examples, processing circuitry 30 may control stimulation generator 34 to deliver one or more recharge pulses after delivery of two or more pulses. In other examples, processing circuitry 30 may control stimulation generator 34 to deliver pulses to promote charge balance on a pulse-by-pulse basis.

In other examples, stimulation generator 34 may deliver different pulses 62 via respective electrode combinations, such that the high pulse density electrical stimulation signal is delivered via multiple therapy programs. For example, under the control of processing circuitry 30, stimulation generator 34 may deliver a series of four pulses with a first electrode combination, and deliver a series of three pulses with a second, different electrode combination. In this example, the series of four pulses can be part of a first sub-signal delivered via the first electrode combination, and the series of three pulses may be part of a second sub-signal delivered via the second electrode combination. The first and second sub-signals, when delivered together over time such that the pulses of the sub-signals are interleaved together (similar to that as shown in FIG. 4A), combine to define high duty cycle electrical stimulation signal 60. Although two sub-signals are used here as an example, in other examples, stimulation generator 34 of IMD 14 may generate and deliver high duty cycle electrical stimulation signal 60 using any suitable number of sub-signals. In some examples, stimulation generator 34 may generate each sub-signal using a respective therapy program, which may be stored as a group in memory 32 of IMD 14 (see FIG. 2).

In some examples in which stimulation generator 34 may deliver different pulses via different electrode combinations, processing circuitry 30 may control stimulation generator 34 may deliver one or more recharge pulses after a predetermined number of pulses are delivered, the predetermined number being greater than one. The predetermined number of pulses may include pulses generated according to different therapy programs. Thus, in some examples, stimulation generator 34 may deliver one or more recharge pulses after pulses of different sub-signals are delivered. For example, under the control of processing circuitry 30, stimulation generator 34 may deliver one or more recharge pulses after stimulation generator delivers a series of two pulses, rather than delivering one or more recharge pulses between each pulse of the series of two pulses, and then again after last pulse of the series of two pulses. In this example, stimulation generator 34 may wait to deliver one or more recharge pulses until after stimulation generator delivers the series of two pulses, rather than delivering one or more recharge pulses between the series of two pulses, and then again after the last pulse of the series of two pulses. In other examples, processing circuitry 30 may control stimulation generator 34 to deliver recharge pulses to balance charge on a pulse-by-pulse basis.

Stimulation generator 34 can deliver the sub-signals using electrodes from a single lead 16A or from two or more leads 16A and 16B. For example, under the control of processing circuitry 30, stimulation generator 34 may deliver a first pulse with electrode 24A of lead 16A together with a housing electrode of outer housing 34 of IMD 14 and deliver pulse a second pulse with electrode 24B of lead 16A together with a housing electrode of outer housing 34 (see FIG. 2). As another example, under the control of processing circuitry 30, stimulation generator 34 may deliver a first pulse with electrodes 24A, 24B of lead 16A and deliver a second pulse with electrodes 24B, 24C of the same lead 16A. In another example, stimulation generator 34 may deliver different pulses with electrodes of different leads. Processing circuitry 30 may, for example, control stimulation generator 34 to alternate delivery of pulses between leads 16A, 16B, or control stimulation generator 34 to otherwise deliver pulses with electrodes of each lead 16A, 16B at different times. For example, under the control of processing circuitry 30, stimulation generator 34 may deliver a first pulse with electrodes 24A, 24B of lead 16A and deliver a second pulse with electrodes 26A, 26B of lead 16B.

Regardless of the number of electrode combinations with which stimulation generator 34 delivers pulses, the combination of pulses may combine to define electrical stimulation signal 60 having a duty cycle in a range of about 9% to about 50% and a frequency in a range of about 1 Hz to about 1400 Hz.

Delivery of each sub-signal by stimulation generator 34 may generate a stimulation field within tissue of the patient, where the stimulation field may be a volume of tissue through which the electrical current from the delivered sub-signal propagates. The electrode combinations with which pulses are delivered and the frequency of high duty cycle electrical stimulation signal 60 can be selected such that any combination of pulses (delivered from any suitable number of different electrode combinations) results in stimulation fields that overlap. The region of overlap of the stimulation fields may be configured to target neural areas responsive to the high (or low) duty cycle mechanisms described herein, e.g., to provide the desired therapeutic effect. In some examples, the regions of the stimulation fields that do not overlap may not provide any therapeutic effect.

In some examples, processing circuitry 30 controls stimulation generator 34 to generate and deliver pulses via two or more therapy programs, each defining a respective electrode combination. For example, some pulses may be part of a first sub-signal defined by a first therapy program and delivered by stimulation generator 34 via a first electrode combination, and other pulses may be part of a second sub-signal defined by a second therapy program and delivered by stimulation generator 34 via a second electrode combination. Stimulation generator 34 may interleave delivery of pulses of the first and second sub-signals, such that the pulses only partially overlap in time or do not overlap in time. Delivery of the first and second sub-signals may generate respective stimulation fields within tissue. In some examples, the stimulation fields, individually and when overlapping, have stimulation intensities less than at least one of: a perception threshold or a paresthesia threshold of the patient. In addition, in some examples, each pulse of the first and second sub-signals has a pulse width less than or equal to about 5 milliseconds, and stimulation generator 34 may interleave delivery of pulses of the first and second sub-signals to deliver electrical stimulation pulses at a frequency in a range of about 1 Hz to about 1400 Hz. In some examples, processing circuitry 30 controls stimulation generator 34 to deliver a recharge signal following the delivery of at least one pulse of each of the first and second electrical sub-signals.

Delivering stimulation signal 60 as multiple sub-signals delivered via respective electrode combinations may help reduce the charge density at the electrode-tissue interface of particular electrodes. In addition, delivering stimulation signal 60 via multiple sub-signals may provide more flexibility in programming the electrical stimulation therapy that has an intensity below the perception or paresthesia threshold intensity level of patient 12 because the sub-signals may each have relatively low stimulation intensities, but due to the overlap in the stimulation fields that may result from the interleaving of the delivery of the sub-signals, the sub-signals may be combined to provide efficacious electrical stimulation therapy to patient 12.

In some examples in which stimulation generator 34 generates and delivers a plurality of sub-signals in order to deliver the electrical stimulation signal having the high duty cycle and frequency less than or equal to about 1400 Hz described herein, stimulation generator 34 may recharge at the end of the pulse train, e.g., after the pulses of the plurality of sub-signals are delivered. In other examples, stimulation generator 34 may recharge after each delivered pulse.

As discussed above, duty cycle may be used to distinguish a low-density or low-dose electrical stimulation signal from a high-density or high-dose electrical stimulation signal. For example, a threshold of 9% may be used to distinguish the low-density electrical stimulation signal 40 of FIG. 4A from the high-density electrical stimulation signal 60 of FIG. 4B. In practice, an end-user may interact with a user interface(s) to program IMD 14 to deliver stimulation that has a form consistent with the low-density electrical stimulation signal 40 of FIG. 4A and the high-density electrical stimulation signal 60. The high-density electrical stimulation signal 60 as discussed however may prematurely deplete or accelerate the depletion of power source 38 of IMD 14. Thus, a cathode-minimized programming algorithm is contemplated to increase the operational lifetime of power source 38 of IMD 14, regardless as to whether power source 38 of IMD 14 is rechargeable or not. An example of a user interface(s) for cathode-minimized stimulation programming is shown in FIGS. 5-6.

Figure 8:
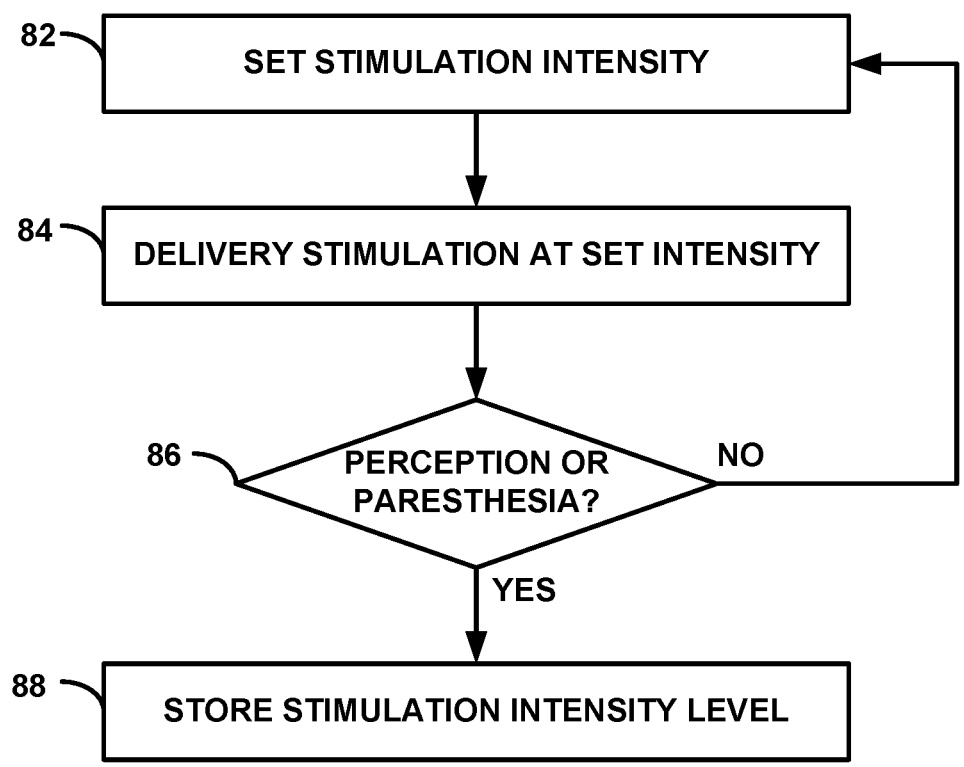
FIG. 8 is a flow diagram that illustrates an example algorithm for determining a perception or paresthesia threshold intensity level for a patient.

For example, FIG. 5 illustrates a user interface 50 for cathode-minimized stimulation programming, whereby the low-density electrical stimulation signal 40 as shown in FIG. 4A may be defined based on program 52 and using an initial electrode configuration (+----+), and then following a process of testing paresthesia coverage over a patient pain pattern using a number of different electrode configurations, a cathode-minimized electrode configuration electrode configuration (+--+) for leads 24, 26 as shown in user interface 50 may be determined, as discussed in further detail below in connection with FIG. 8. The cathode-minimized electrode configuration electrode configuration is an electrode configuration determined to induce paresthesia over a patient pain pattern at electrical stimulation parameter settings within the low-density electrical stimulation range and using a fewest number of cathodes (i.e., 2 cathodes per lead in this instance). Minimizing the number of cathodes directly translates into more efficient use of battery power because a cathode typically draws about 4× as much power from a battery as compared to an anode. As shown, the program 52 is defined such that amplitude $AMP_A$ is equal to 1.5 V, pulse width $PW_A$ is equal to 450 microseconds, and the number of pulses per second of the low-density electrical stimulation signal 40 that exhibit the amplitude $AMP_A$ and pulse width $PW_A$ is equal to 80 (i.e., 80 Hz). As shown above, duty cycle of such a signal=3.6%.

In contrast with FIG. 5, FIG. 6 illustrates a user interface 62 for cathode-minimized stimulation programming, whereby the high-density electrical stimulation signal 60 as shown in FIG. 4B may be defined based on program 64 and using the electrode configuration (+--+) for leads 24, 26 (see FIG. 2, in an embodiment where each one of leads 24, 26 exhibits 8 electrodes) determined to induce paresthesia over a patient pain pattern at electrical stimulation parameter settings within the low-density electrical stimulation range and using the fewest number of cathodes (i.e., 2 cathodes as defined above in connection with FIG. 5). In particular, the program 64 is defined such that amplitude $AMP_B$ is equal to 1.7 V, pulse width $PW_B$ is equal to 90 microseconds, and the number of pulses per second of the low-density electrical stimulation signal 40 that exhibit the amplitude $AMP_{A1}$ and pulse width $PW_{A1}$ is equal to 1000. As shown above, duty cycle of such a signal=9%, a high-density electrical stimulation signal.

As discussed above, the electrical stimulation parameter values with which IMD 14 may generate and deliver low-density electrical stimulation and high-density electrical stimulation described herein, grouped together having a duty cycle of about 2% to about 50%, a frequency in a range of about 1 Hz to about 1400 Hz (e.g., less than or equal to about 1000 Hz), and a pulse width of about 5 ms or less, and may be selected using any suitable technique.

Figure 7:
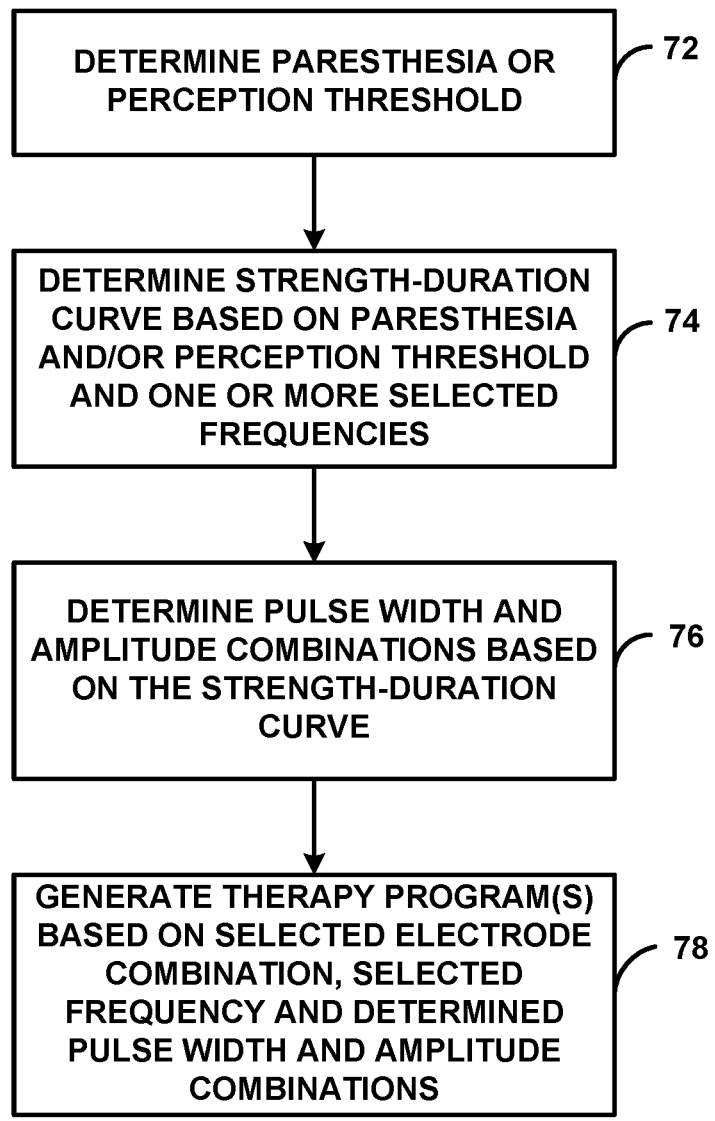
FIG. 7 is a flow diagram that illustrates an example algorithm for programming low-density or high-density electrical stimulation therapy having a stimulation intensity level that is less than a perception or paresthesia threshold intensity level for a patient.

FIG. 7 is a flow diagram of an example technique 70 for selecting the electrical stimulation parameter values. While FIG. 7 is described with respect to processing circuitry 50 of programmer 18, in other examples, processing circuitry 30 of IMD 14 may perform any part of the technique described with respect to FIG. 7, alone or in combination with processing circuitry 50 of programmer 18.

In the technique shown in FIG. 7, processing circuitry 50 determines a paresthesia or perception threshold intensity level for patient 12 (72), e.g., using the technique described below with respect to FIG. 8, by retrieving a stored paresthesia or perception threshold intensity level from memory 52 (see FIG. 2), or by receiving a paresthesia or perception threshold intensity level from another device, e.g., IMD 14. Processing circuitry 50 may, for example, determine the paresthesia threshold (72), determine the perception threshold (72), determine the lower of the paresthesia threshold intensity level or the perception threshold intensity level for patient 12 (72), or determine the higher of the paresthesia threshold intensity level or the perception threshold intensity level for patient 12.

A paresthesia threshold intensity level may be a lowest determined electrical stimulation intensity level at which patient 12 first perceives paresthesia from the electrical stimulation delivered by IMD 14. A perception threshold intensity level may be a lowest determined electrical stimulation intensity level at which patient 12 first perceives the electrical stimulation delivered by IMD 14. In some cases, depending on the patient and/or the target electrical stimulation site within the patient, the patient may first perceive the electrical stimulation delivered by IMD 14 as paresthesia. Thus, in some cases, the perception threshold intensity level may be substantially the same (e.g., identical or nearly identical) as the paresthesia threshold intensity level. In other cases, however, a patient may first perceive the electrical stimulation as a sensation different than paresthesia. Thus, some cases, the perception threshold intensity level may be different than the paresthesia threshold intensity level. In these examples, a clinician may program IMD 14 and/or programmer 18 to use either the perception or paresthesia threshold intensity levels to select the electrical stimulation parameter with the technique shown in FIG. 7.

After determining one or both of the paresthesia threshold intensity level or the perception threshold intensity level, processing circuitry 50 may determine a strength-duration curve based on the determined one or both of the paresthesia or perception threshold intensity level and one or more selected electrical stimulation signal frequencies (74). A strength-duration curve may describe the relationship between a strength of electrical stimulation and duration, e.g., for a particular physiological response, such as a response below the paresthesia or perception threshold of patient 12. The strength of electrical stimulation may be a function of, for example, any one or more of the voltage or current amplitude value of the stimulation signal, frequency of stimulation signals, signal duration (e.g., pulse width in the case of stimulation pulses), duty cycle, and the like.

An example of a strength duration curve is an amplitude-pulse width curve. The amplitude-pulse width curve may reflect, for a selected stimulation frequency, different combinations of amplitude and pulse width values that contribute to a stimulation field in a substantially similar manner. For example, the amplitude-pulse width curve may indicate that a first electrical stimulation signal with a first amplitude and a first pulse width, and a second electrical stimulation signal having a higher amplitude pulse with a shorter pulse width (i.e., shorter than the first pulse width) may both provide electrical stimulation therapy below the paresthesia or perception threshold of patient 12. Each position on the amplitude-pulse width curve, or each position within a particular range of positions along the amplitude-pulse width curve, may result in a substantially similar stimulation energy when the other therapy parameter values, such as a frequency, remain substantially constant (e.g., the other therapy parameter values may remain within a particular range of therapy parameter values, such as within a 10% window or less from the values defined by the therapy program). Thus, for a given stimulation frequency, the amplitude-pulse width curve may define, e.g., via the amplitude-pulse width combinations associated with the area under the curve and/or along the curve, the amplitude and pulse width combinations that provide electrical stimulation therapy having an intensity level below the paresthesia or perception threshold intensity level of patient 12.

For a given frequency (e.g., in a range of about 1 Hz to about 1000 Hz), based on the strength-duration curve, processing circuitry 50 may determine the pulse width and amplitude combination that provides efficacious electrical stimulation therapy to patient 12 and also has a stimulation intensity below the paresthesia or perception threshold of patient 12 (76). Processing circuitry 50 may, in response to user input provided via programmer 18, control stimulation generator 34 to generate and deliver electrical stimulation therapy to patient 12 with the frequency associated with the strength-duration curve, a selected combination of electrodes 24, 26, and a plurality of pulse width and amplitude combinations along the strength-duration curve or below the amplitude-pulse width curve. Processing circuitry 50 may determine whether any of the selected pulse width and amplitude combinations provides efficacious electrical stimulation therapy for patient 12, e.g., based on patient 12 input or input from another entity received via programmer 18, based on input from a sensing module of IMD 14 or a separate sensing module, or any combination thereof. Processing circuitry 50 may generate one or more therapy programs based on the one or more pulse width and amplitude combinations that provide efficacious electrical stimulation therapy to patient 12, together with the selected frequency and electrode combination (78).

In some examples in which stimulation generator 34 generates and delivers low duty cycle electrical stimulation therapy or high duty cycle electrical stimulation therapy via a plurality of sub-signals delivered via respective electrode combinations, processing circuitry 50 may determine a strength-duration curve for each electrode combination. Thus, for each electrode combination, the respective strength-duration curve may indicate a plurality of combinations of electrical stimulation parameters (e.g., amplitude and pulse width for a given frequency) that provide a charge per pulse below the paresthesia or perception threshold of patient 12. Based on the strength-duration curves, processing circuitry 50, alone or based on input from a clinician, may determine, for each of the electrode combinations, one or more therapy programs that provide a relatively low charge or high charge per pulse (e.g., the relatively lowest or highest charge per pulse that remains at or below the paresthesia or perception threshold of patient 12). Each therapy program may define a sub-signal. Processing circuitry 50, alone or based on input from a clinician, may then determine a frequency to interleave the two or more sub-signals.

In some examples, to determine the therapy programs, processing circuitry 50 may determine one or more test therapy programs that define relatively wide pulse widths and relatively low frequencies of the sub-signals, control stimulation generator 34 to generate and deliver electrical stimulation to patient 12 according to the test therapy programs, and, if the delivered electrical stimulation therapy is not sufficiently efficacious, processing circuitry 50 may modify one or more of the test therapy programs until the electrical stimulation provides efficacious stimulation therapy for patient 12. The efficacy of the electrical stimulation therapy can be based on input from patient 12, from one or more sensed physiological parameters, or any combination thereof. Processing circuitry 50 may modify one or more of the test therapy programs by, for example, incrementally narrowing the pulse width (e.g., by a predetermined increment) and/or incrementally increasing the frequency (e.g., by a predetermined increment).

Processing circuitry 50 may store the one or more therapy programs 41, 43 in memory 52 or a memory of another device for later delivery of electrical stimulation therapy to patient 12. Processing circuitry 50 may control stimulation generator 34 to generate and deliver electrical stimulation therapy to patient 12 in accordance with the one or more therapy programs 41, 43.

In some cases, therapeutic efficacy of electrical stimulation therapy delivered by IMD 14 may change as the patient posture state (e.g., a particular patient posture or a combination of posture and activity) changes. Efficacy may refer to a combination of complete or partial alleviation of symptoms alone, or in combination with no side effects or an acceptable or tolerable degree of undesirable side effects. In some examples, processing circuitry 30 of IMD 14 or processing circuitry 50 of programmer 18 may be configured to adjust one or more therapy parameter values based on different postures and/or activities engaged by patient 12 to maintain effective therapy, e.g., by selecting select different therapy programs based on a posture state of patient 12. In these examples, processing circuitry 30, 50 may determine the paresthesia or perception threshold of patient 12 for each of a plurality of different posture states and determine one or more therapy programs 40 for each of the posture states using the technique shown in FIG. 7 based on the respective paresthesia or perception threshold.

FIG. 8 is a flow diagram of an example technique 80 by which processing circuitry 30 of IMD 14 can determine at least one of the perception or paresthesia threshold intensity level for patient 12. In some examples, processing circuitry 30 is configured to determine the perception threshold intensity level, while in other examples, processing circuitry 30 is configured to determine the paresthesia threshold intensity level or both the perception and paresthesia threshold intensity level.

The perception or paresthesia threshold intensity level can be patient-specific, as well as specific to a target tissue site within patient 12. Thus, a perception or paresthesia threshold intensity level can be determined for each target tissue site to which IMD 14 delivers stimulation therapy. In some examples, processing circuitry 30 of programmer 18 may implement the technique illustrated in FIG. 8 automatically, e.g., without user intervention or control after initiating the technique. In other examples, processing circuitry 30 may implement the technique illustrated in FIG. 8 under control of a user, such as a clinician, who controls processing circuitry 30 via programmer 18. While FIG. 8 is described with respect to processing circuitry 30 of IMD 14, in other examples, processing circuitry 50 of programmer 18 may perform any part of the technique described with respect to FIG. 9, alone or in combination with processing circuitry 30 of IMD 14.

In accordance with the technique shown in FIG. 8, processing circuitry 30 sets stimulation parameter values such that the stimulation parameter values define a relatively low stimulation intensity, e.g., an intensity below an expected perception or paresthesia threshold intensity (82) The initial stimulation parameter values may be selected by a clinician in some examples. In some examples in which processing circuitry 30 controls stimulation generator 34 to generate and deliver stimulation to patient 12 in the form of electrical pulses, the stimulation parameters include at least one of a voltage or current amplitude, a pulse width, a pulse rate, or a duty cycle. In examples in which processing circuitry 30 controls stimulation generator 34 to deliver stimulation to patient 12 in the form of a continuous waveform, the stimulation parameters include at least one of a voltage amplitude, a current amplitude, a frequency, a waveform shape, or a duty cycle.

In either case, processing circuitry 30 sets the stimulation parameters to respective values to define a stimulation intensity, and controls stimulation generator 34 to deliver stimulation to patient 12 at the set stimulation intensity (defined by the selected stimulation parameter values) (84). During therapy delivery or after stimulation generator 34 delivers stimulation to patient 12, processing circuitry 30 determines whether patient 12, a clinician, or patient caretaker has provided input indicating patient 12 has perceived the electrical stimulation or indicating paresthesia resulted from the electrical stimulation (84). Patient 12, the clinician, or patient caretaker can provide the input, e.g., via user interface 54 of programmer 18 or directly via IMD 14. For example, a motion sensor can be integrated into or on a housing of IMD 14, and the motion sensor can be configured to generate a signal that is indicative of patient 12 tapping IMD 14 through the skin. The number, rate, or pattern of taps may be associated with the input indicative of stimulation perception or paresthesia, and processing circuitry 30 may identify the tapping by patient 12 to determine when patient input is received. When the input is received via user interface 54 of programmer 18, processing circuitry 50 of programmer 18 may transmit a signal indicative of the input to IMD 14 via the respective telemetry modules 56, 36.

When processing circuitry 30 has not received an indication of the input indicative of the stimulation perception or paresthesia within a predetermined time period during or immediately after delivery of the stimulation according to the selected stimulation intensity ("NO" branch of block 86), processing circuitry 30 again sets the stimulation intensity, e.g., by adjusting at least one stimulation parameter value to increase a stimulation intensity of the stimulation signal (82). For example, processing circuitry 30 may increase a voltage amplitude or a current amplitude to increase the stimulation intensity. In some examples, processing circuitry 30 changes a value of only one of the stimulation parameters while the remaining parameters are kept approximately constant. The stimulation parameter that is selected may be known to affect stimulation intensity. In other examples, processing circuitry 30 may adjust a combination of two or more stimulation parameters to increase stimulation intensity.

After modifying the one or more stimulation parameter values, processing circuitry 30 controls stimulation generator 34 to deliver stimulation to patient 12 using the newly defined stimulation parameter values (84). In this way, processing circuitry 30 can implement an iterative procedure to determine the perception or paresthesia threshold intensity for patient 12, and, in some examples, for a specific target tissue site within patient 12.

In response to not receiving input indicative of patient perception or paresthesia is received within a predetermined time period during or immediately after delivery of the stimulation according to the selected stimulation intensity ("NO" branch of block 86), processing circuitry 30 may again adjust at least one stimulation parameter value to increase a stimulation intensity of the stimulation signal (82). This process may repeat until processing circuitry 30 receives input indicative of patient perception or paresthesia within a predetermined time period during or immediately after delivery of the stimulation according to the selected stimulation intensity. In response to receiving the input ("YES" branch of block 86), processing circuitry 30 may store the stimulation intensity level as the patient perception threshold intensity level and/or paresthesia threshold intensity level (depending on the whether the response indicates patient perception of the electrical stimulation or resulting paresthesia, respectively) in memory 32 of IMD 14 (FIG. 2) or in another memory (e.g., memory 52 of programmer 18) (88).

In addition, processing circuitry 30 may define stimulation parameter values for the therapy programs 41, 43 (see FIG. 2) for providing the low or high duty cycle electrical stimulation techniques described herein based on the determined patient perception threshold intensity level and/or paresthesia threshold intensity level, e.g., using the technique described with respect to FIG. 7. For example, processing circuitry may define stimulation parameter values for the therapy programs 41, 43 (see FIG. 2) that result in a stimulation intensity level less than or equal to one or both of the patient perception threshold intensity level or paresthesia threshold intensity level.

Figure 9:
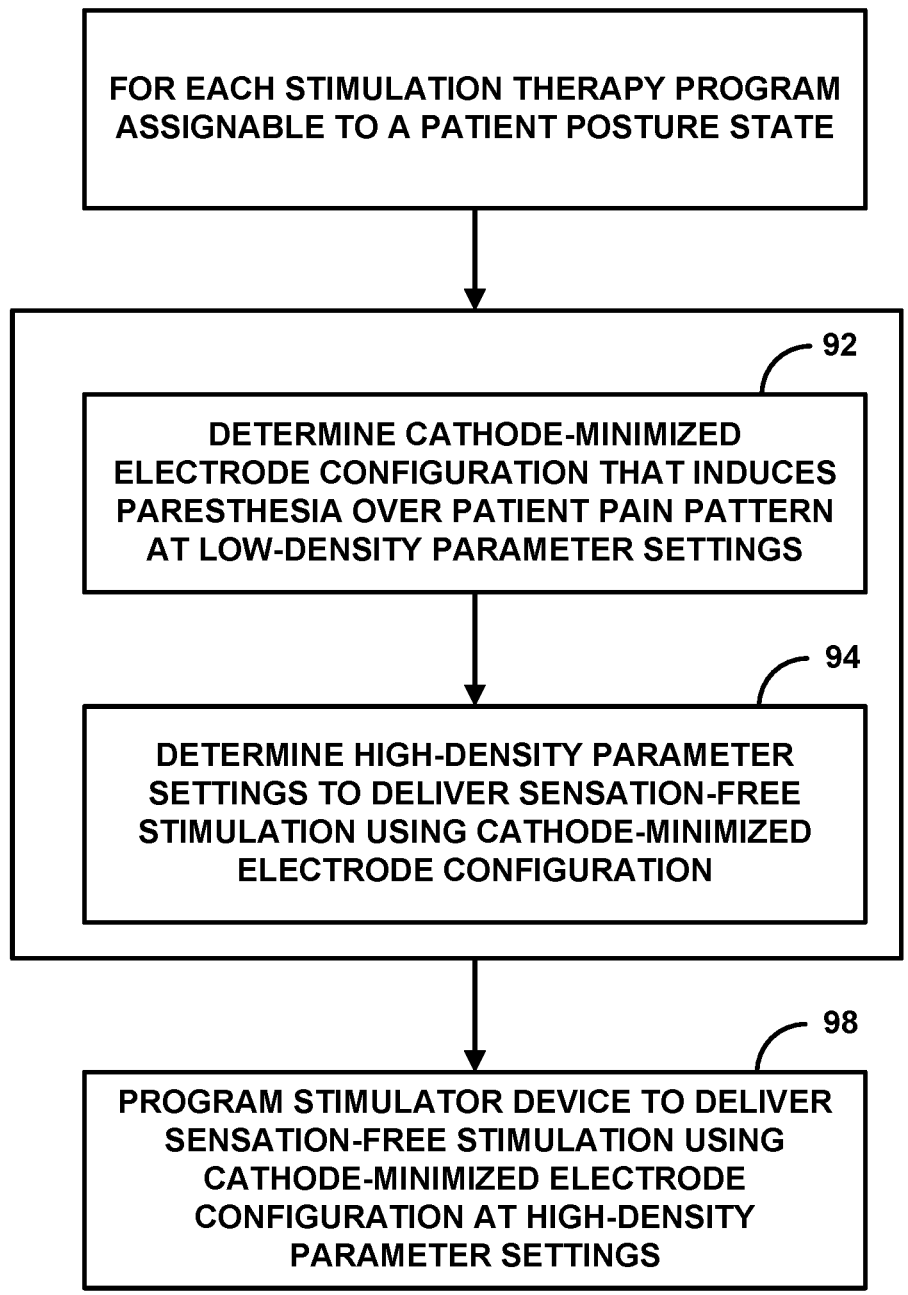
FIG. 9 is a flow diagram that illustrates an example algorithm for cathode-minimized stimulation programming.
Figure 10:
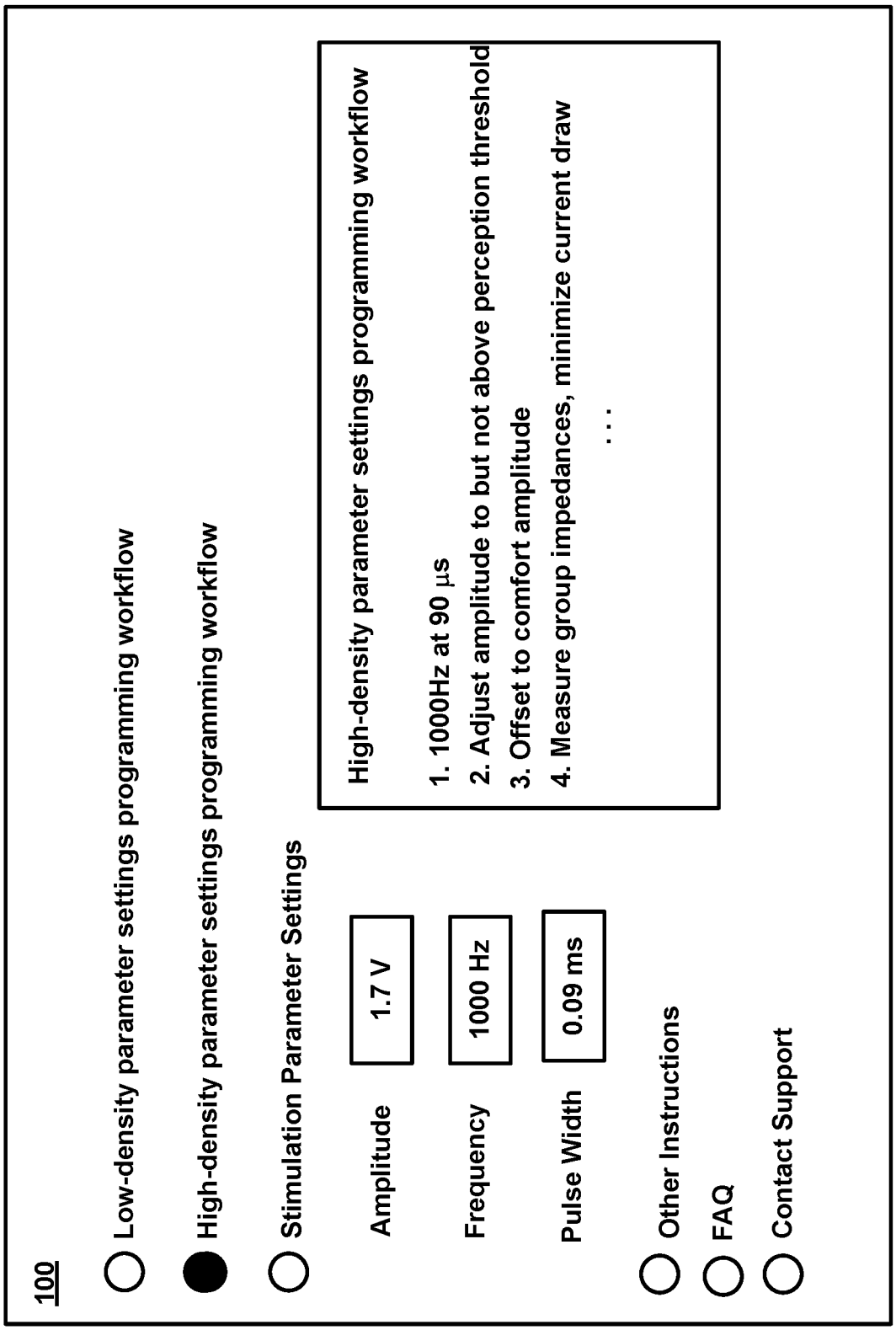
FIG. 10 illustrates another example user interface for cathode-minimized stimulation programming.

While the methods of FIGS. 7 and 8 are described primarily from the perspective of the IMD 14, the same techniques may in general be manually performed. In addition, an algorithm for programming the IMD 14 to deliver stimulation therapy at high-density parameter settings using a cathode-minimized electrode configuration determined to induce paresthesia over a patient pain pattern at low-density parameter settings may in general be performed manually or in part by the IMD 14 in the absence of human intervention. FIG. 9 illustrates an example algorithm for cathode-minimized stimulation programming. FIG. 10 illustrates a user interface for cathode-minimized stimulation programming.

With reference to FIG. 9, steps of the algorithm for cathode-minimized stimulation programming may include: for each programmable patient posture position (i.e., for each programmable therapy program that is assignable to a particular posture state of patient 12), determining a cathode-minimized electrode configuration that induces paresthesia over patient pain pattern at low-density parameter settings (92) and determining high-density parameter settings to deliver sensation-free stimulation using cathode-minimized electrode configuration (94); and programming a stimulator device (e.g., IMD 14) to deliver sensation-free stimulation using cathode-minimized electrode configuration at high-density parameter settings (96).

With reference to FIG. 10, various steps for performing the algorithm for cathode-minimized stimulation programming of FIG. 9 may be output for display within an interactive user interface 100 by the programmer device 18 (see FIG. 3). In general, a user may interact with the interactive user interface 100 to access instructions associated with each one of the step 92-96 as shown in FIG. 9, and further may interact with the interactive user interface 100 to in real-time program amplitude, frequency, and pulse width settings for delivery of low-density and high-density electrical stimulation by the IMD 14, similar to that shown and discussed above in connection with FIGS. 5-6. Other functionality may be accessed via the interactive user interface 100 through user interaction with an "Other Instructions" button an "FAQ" button and a "Contact Support" button. The present disclosure however is not so limited, and it is contemplated that the interactive user interface 100 may be developed such that any particular functionality that may facilitate the features or aspects of the present disclosure may be built-in to the user interface 100 to enable an end user to leverage the particular functionality.

With reference to both FIGS. 9 and 10, details of an example algorithm for cathode-minimized stimulation programming, of which instructions may be accessible through user interaction with an "Low-density parameter settings programming workflow" button and a "High-density parameter settings programming workflow" button, may include:

Low-density parameter settings programming workflow: Once the IMD 14 is interrogated, execute an electrode impedance measurement to determine if any electrodes of the leads 24, 26 are out of range. If an electrode of the leads 24, 26 is out of range, then increase the voltage from default to a voltage tolerable by the subject, e.g., from 0.7 V to 1.5 V or 3.0 V if tolerable to the subject. This will help identify if there are any electrodes of the leads 24, 26 that should be avoided for use in stimulation therapy (e.g., <50 Ohms at 0.7 V, <50 Ohms at 1.5 V, and <150 Ohms at 3.0 V).

Low-density parameter settings programming workflow: Program with the mindset of utilizing any of the 16 electrodes of the leads 24, 26 (in an embodiment where each one of leads 24, 26 includes 8 electrodes) needed to obtain paresthesia in the seated position. Start the programming session using low-density stimulation parameters (e.g., 450 microseconds, 80 Hz) with the electrodes 2-5 electrodes (+−−+) in the middle of the lead 24 or 26 closest to midline (if bilateral pain), as shown in FIG. 5. If the subject has unilateral pain start with the lead 24 or 26 that is on the side of the pain pattern (i.e. left lead 24 for left sided pain or right lead 26 for right sided coverage).

Low-density parameter settings programming workflow: Slowly increase stimulation amplitude to just under the maximum uncomfortable intensity the subject can tolerate to demonstrate ample paresthesia coverage over the pain pattern. In general, comfortable paresthesia is not the intent and in many cases paresthesia will be experienced in areas typically associated with undesirable stimulation, such as to the ribs and stomach.

Low-density parameter settings programming workflow: If ample paresthesia coverage of the entire pain pattern is achieved (in addition to paresthesia to other areas), then decrease the number of cathodes and retest paresthesia coverage. According to the principles of the present disclosure, the goal is to utilize the lowest number of cathodes while still obtaining paresthesia over their individual pain pattern. If paresthesia does not cover the pain pattern, use anodes to shape the field or if needed increase the cathodes to 3 maximum if possible.

High-density parameter settings programming workflow: Once the cathode-minimized electrode configuration using low-density stimulation parameters determined, then modify the width and rate of the stimulation signal to high-density stimulation parameters. For example, start with 1000 Hz and 90 microseconds as shown in FIG. 6.

High-density parameter settings programming workflow: After the rate and width parameters are adjusted, then increase the amplitude to the lowest perception threshold and then lower the amplitude by 0.3 V (e.g., to 2 V and then decrease to 1.7 V as shown in FIG. 6), which is the "comfort amplitude" that the subject will be programmed to.

Low- and High-density parameter settings programming workflow: Repeat one or more of the prior steps for all adaptive stimulation position amplitude limits to make the "comfort amplitude" the maximum amplitude for each programmable therapy program that is assigned to a particular posture state of patient 12. Another alternative could be to utilize the programmer device 18 to maintain the "comfort amplitude" at all times.

High-density parameter settings programming workflow: Once the comfort amplitude is determined, measure group impedances for each programmable therapy program using high-density stimulation parameters that is assigned to a particular posture state of patient 12 and analyze the current draw (mA) data. The group output (current, mA) should be targeted for as low as possible, such as less than 15-20 mA. The lower the group output (current, mA), the less power draw the battery of the IMD 14 will experience and the recharge intervals will increase. To lower the group output (current, mA), adjust the amplitude voltage with consideration given as to whether the amplitude voltage is sufficient in terms of efficacy.

Additionally, or alternatively, details of an example algorithm for cathode-minimized stimulation programming, of which instructions may be accessible through user interaction with an "Low-density parameter settings programming workflow" button and a "High-density parameter settings programming workflow" button, may include:

Low- and High-density parameter settings programming workflow: Instructions for transmitting data to a stimulator device to program the stimulator device to deliver stimulation therapy at high-density parameter settings using a cathode-minimized electrode configuration determined to induce paresthesia over a patient pain pattern at low-density parameter settings.

Low- and High-density parameter settings programming workflow: Instructions for programming a stimulator device to deliver stimulation therapy at high-density parameter settings using a cathode-minimized electrode configuration determined to induce paresthesia over a patient pain pattern at low-density parameter settings.

Low- and High-density parameter settings programming workflow: Instructions for programming a stimulator device to deliver stimulation therapy at high-density parameter settings using a cathode-minimized electrode configuration determined to induce paresthesia over a patient pain pattern at sub-threshold high-density parameter settings.

Low- and High-density parameter settings programming workflow: Instructions for programming a stimulator device to deliver stimulation therapy at first pulse density parameter settings using a cathode-minimized electrode configuration determined to induce paresthesia over a patient pain pattern at second pulse density parameter settings.

Low- and High-density parameter settings programming workflow: Instructions for programming a stimulator device to deliver stimulation therapy at first charge density parameter settings using a cathode-minimized electrode configuration determined to induce paresthesia over a patient pain pattern at second charge density parameter settings.

Low-density parameter settings programming workflow: Instructions for determining a cathode-minimized configuration, of a stimulator device configured to deliver electrical stimulation via a plurality of electrodes, of the plurality of electrodes that induces paresthesia over a patient pain pattern at electrical stimulation parameter settings within a first duty cycle range.

High-density parameter settings programming workflow: Instructions for determining electrical stimulation parameter settings within a second duty cycle range for the stimulator device to deliver non-paresthesia inducing electrical stimulation that at least partially suppresses the pain pattern using the cathode-minimized configuration of the plurality of electrodes.

High-density parameter settings programming workflow: Instructions for transmitting data to the stimulator device to program the stimulator device to deliver non-paresthesia inducing electrical stimulation at determined parameter settings within the second duty cycle range using the cathode-minimized configuration of the plurality of electrodes.

Low- and High-density parameter settings programming workflow: Instructions for determining that duty cycle within the first duty cycle range is greater than duty cycle in the second duty cycle range.

Low- and High-density parameter settings programming workflow: Instructions for determining that pulse or charge density within the first duty cycle range is less than pulse or charge density within the second duty cycle range.

Low-density parameter settings programming workflow: Instructions for providing user input specifying the cathode-minimized configuration of the plurality of electrodes in response to the instructions for determining the cathode-minimized configuration.

Low-density parameter settings programming workflow: Instructions for transmitting data to the stimulator device to program the stimulator device to deliver electrical stimulation at parameter settings within the first duty cycle range using the cathode-minimized stimulation configuration of the plurality of electrodes.

Low-density parameter settings programming workflow: Instructions for performing an impedance measurement to identify electrically-isolated electrodes of the plurality of electrodes and for performing an amplitude adjustment to identify ones of the electrically-isolated electrodes to be excluded from the cathode-minimized configuration.

Low-density parameter settings programming workflow: Instructions for determining that the cathode-minimized configuration comprises a number of anodes greater than or equal to a number of cathodes.

Low-density parameter settings programming workflow: Instructions for determining that the cathode-minimized configuration comprises a number of cathodes that is less than or equal to three cathodes.

Low-density parameter settings programming workflow: Instructions for programming an initial electrode configuration that induces paresthesia over at least one of a left lateral or a right lateral patient pain pattern.

Low-density parameter settings programming workflow: Instructions for increasing stimulation amplitude to a supra-perception threshold intensity.

Low-density parameter settings programming workflow: Instructions for testing paresthesia coverage over the patient pain pattern for a number of different electrode configurations that are addressable by the stimulator device and that exhibit a different number of cathodes.

Low-density parameter settings programming workflow: Instructions for providing user input specifying at least one of the number of different electrode configurations in response to the instructions for testing paresthesia coverage.

Low-density parameter settings programming workflow: Instructions for testing paresthesia coverage over the patient pain pattern for a number of different electrode configurations that are addressable by the stimulator device and that exhibit a different number of anodes but a same number of cathodes.

Low-density parameter settings programming workflow: Instructions for providing user input specifying at least one of the number of different electrode configurations in response to the instructions for testing paresthesia coverage.

Low-density parameter settings programming workflow: Instructions for testing paresthesia coverage over the patient pain pattern for a number of different electrode configurations that are addressable by the stimulator device and that exhibit a different number of anodes but a same number of cathodes.

Low-density parameter settings programming workflow: Instructions for providing user input specifying at least one of the number of different electrode configurations in response to the instructions for testing paresthesia coverage.

Low-density parameter settings programming workflow: Instructions for programming, for the first duty cycle range, stimulation frequency to a value less than or equal to 1200 Hz and for programming stimulation pulse width to a value less than or equal to 1000 µs.

High-density parameter settings programming workflow: Instructions for programming, for the second duty cycle range, stimulation frequency to a value less than or equal to 1200 Hz and for programming stimulation pulse width to a value less than or equal to 1000 µs.

Low- and High-density parameter settings programming workflow: Instructions for adjusting perceived stimulation sensation from perceptible to imperceptible.

Low- and High-density parameter settings programming workflow: Instructions for adjusting perceived stimulation sensation from imperceptible to perceptible.

High-density parameter settings programming workflow: Instructions for programming the stimulator device to deliver non-paresthesia inducing electrical stimulation at determined parameter settings within the second duty cycle range using the cathode-minimized configuration of the plurality of electrodes and at a stimulation amplitude that is determined based upon a signal received from posture state circuitry.

While the techniques described above are primarily described as being performed by processing circuitry 30 of IMD 14 or processing circuitry 50 of programmer 18, in other examples, one or more other processors may perform any part of the techniques described herein alone or in addition to processing circuitry 30 or processing circuitry 50. Thus, reference to "a processor" may refer to "one or more processors." Likewise, "one or more processors" may refer to a single processor or multiple processors in different examples.

The techniques described in this disclosure, including those attributed to IMD 14, programmer 18, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method comprising:
    by a programmer device configured to program a stimulator device to deliver electrical stimulation via a plurality of electrodes:
        outputting for display instructions for determining a cathode-minimized configuration of the plurality of electrodes that induces paresthesia over a patient pain pattern at electrical stimulation parameter settings within a first duty cycle range, wherein determining the cathode-minimized configuration comprises:
            controlling the stimulator device to execute an electrode impedance measurement to determine a set of electrodes of the plurality of electrodes to use to deliver electrical stimulation, wherein the set of electrodes comprises a number of cathodes;
            adjusting a stimulation amplitude of the set of electrodes to induce paresthesia over the patient pain pattern using the set of electrodes; and
            decreasing the initial number of cathodes in the set of electrodes until the set of electrodes comprises a minimum number of cathodes that induces paresthesia over the patient pain pattern;
        outputting for display instructions for determining electrical stimulation parameter settings within a second duty cycle range for the stimulator device to deliver non-paresthesia inducing electrical stimulation that at least partially suppresses the pain pattern using the cathode-minimized configuration of the plurality of electrodes; and
        transmitting data to the stimulator device to program the stimulator device to deliver non-paresthesia inducing electrical stimulation at determined parameter settings within the second duty cycle range using the cathode-minimized configuration of the plurality of electrodes.

2. The method of claim 1, wherein duty cycle within the first duty cycle range is greater than duty cycle in the second duty cycle range.

3. The method of claim 1, wherein pulse or charge density within the first duty cycle range is less than pulse or charge density within the second duty cycle range.

4. The method of claim 1, wherein outputting for display instructions for determining the cathode-minimized configuration of the plurality of electrodes that induces paresthesia over the patient pain pattern at electrical stimulation parameter settings within the first duty cycle range comprises:
    receiving user input specifying the cathode-minimized configuration of the plurality of electrodes in response to the instructions for determining the cathode-minimized configuration; and
    transmitting data to the stimulator device to program the stimulator device to deliver electrical stimulation at parameter settings within the first duty cycle range using the cathode-minimized stimulation configuration of the plurality of electrodes.

5. The method of claim 1, further comprising:
    outputting for display instructions for performing an impedance measurement to identify electrically-isolated electrodes of the plurality of electrodes and for performing an amplitude adjustment to identify ones of the electrically-isolated electrodes to be excluded from the cathode-minimized configuration.

6. The method of claim 1, wherein the cathode-minimized configuration comprises a number of anodes greater than or equal to a number of cathodes.

7. The method of claim 1, wherein outputting for display instructions for determining the cathode-minimized configuration of the plurality of electrodes that induces paresthesia over the patient pain pattern at electrical stimulation parameter settings within the first duty cycle range comprises:
    outputting for display instructions for testing paresthesia coverage over the patient pain pattern for a number of different electrode configurations that are addressable by the stimulator device and that exhibit a different number of cathodes; and
    receiving user input specifying at least one of the number of different electrode configurations in response to the instructions for testing paresthesia coverage.

8. The method of claim 1, wherein outputting for display instructions for determining the cathode-minimized configuration of the plurality of electrodes that induces paresthesia over the patient pain pattern at electrical stimulation parameter settings within the first duty cycle range comprises:
    outputting for display instructions for testing paresthesia coverage over the patient pain pattern for a number of different electrode configurations that are addressable by the stimulator device and that exhibit a different number of cathodes but a same number of anodes; and
    receiving user input specifying at least one of the number of different electrode configurations in response to the instructions for testing paresthesia coverage.

9. The method of claim 1, wherein outputting for display instructions for determining the cathode-minimized configuration of the plurality of electrodes that induces paresthesia over the patient pain pattern at electrical stimulation parameter settings within the first duty cycle range comprises:
    outputting for display instructions for programming stimulation frequency to a value less than or equal to 1200 Hz and for programming stimulation pulse width to a value less than or equal to 1000 μs.

10. The method of claim 1, wherein outputting for display instructions for determining electrical stimulation parameter settings within the second duty cycle range for the stimulator device to deliver non-paresthesia inducing electrical stimulation that at least partially suppresses the pain pattern using the cathode-minimized configuration of the plurality of electrodes comprises:
  outputting for display instructions for programming stimulation frequency to a value less than or equal to 1200 Hz and for programming stimulation pulse width to a value less than or equal to 1000 μs.

11. A programmer device configured to program a stimulator device to deliver electrical stimulation via a plurality of electrodes, comprising:
  telemetry circuitry;
  a user interface configured to:
    output for display instructions for determining a cathode-minimized configuration of the plurality of electrodes that induces paresthesia over a patient pain pattern at electrical stimulation parameter settings within a first duty cycle range;
    output for display instructions for determining electrical stimulation parameter settings within a second duty cycle range for the stimulator device to deliver non-paresthesia inducing electrical stimulation that at least partially suppresses the pain pattern using the cathode-minimized configuration of the plurality of electrodes; and
  processing circuitry configured to:
    determine the cathode-minimized configuration of the plurality of electrodes by:
      controlling the stimulator device to execute an electrode impedance measurement to determine a set of electrodes of the plurality of electrodes to use to deliver electrical stimulation, wherein the set of electrodes comprises a number of cathodes;
      adjusting a stimulation amplitude of the set of electrodes to induce paresthesia over the patient pain pattern using the set of electrodes; and
      decreasing the initial number of cathodes in the set of electrodes until the set of electrodes comprises a minimum number of cathodes that induces paresthesia over the patient pain pattern; and
    control the telemetry circuitry to transmit data to the stimulator device to program the stimulator device to deliver non-paresthesia inducing electrical stimulation at determined parameter settings within the second duty cycle range using the cathode-minimized configuration of the plurality of electrodes.

12. The programmer device of claim 11, wherein duty cycle within the first duty cycle range is greater than duty cycle within the second duty cycle range.

13. The programmer device of claim 11, wherein pulse or charge density within the first duty cycle range is less than pulse or charge density within the second duty cycle range.

14. The programmer device of claim 11, wherein:
  the user interface is configured to:
    receive user input specifying the cathode-minimized configuration of the plurality of electrodes in response to the instructions for determining the cathode-minimized configuration; and
  the processing circuitry is configured to:
    transmit data to the stimulator device to program the stimulator device to deliver electrical stimulation at parameter settings within the first duty cycle range using the cathode-minimized stimulation configuration of the plurality of electrodes.

15. The programmer device of claim 11, wherein the user interface is configured to output for display instructions for performing an impedance measurement to identify electrically-isolated electrodes of the plurality of electrodes and for performing an amplitude adjustment to identify ones of the electrically-isolated electrodes to be excluded from the cathode-minimized configuration.

16. The programmer device of claim 11, wherein the cathode-minimized configuration comprises a number of cathodes that is less than or equal to three cathodes.

17. The programmer device of claim 11, wherein the user interface is configured to output for display instructions for programming an initial electrode configuration that induces paresthesia over at least one of a left lateral or a right lateral patient pain pattern.

18. The programmer device of claim 11, wherein the user interface is configured to output for display instructions for increasing stimulation amplitude to a supra-perception threshold intensity.

19. The programmer device of claim 11, wherein the user interface is configured to output for display instructions for programming stimulation frequency to a value less than or equal to 1200 Hz and for programming stimulation pulse width to a value less than or equal to 1000 μs.

20. The programmer device of claim 11, wherein the user interface is configured to output for display instructions for adjusting perceived stimulation sensation from perceptible to imperceptible and instructions for adjusting perceived stimulation sensation from imperceptible to perceptible.

21. A non-transitory computer-readable storage medium comprising program instructions that, when executed by processing circuitry of a programmer device configured to program a stimulator device to deliver electrical stimulation via a plurality of electrodes, cause the programmer device to:
  output for display instructions for determining a cathode-minimized configuration of the plurality of electrodes that induces paresthesia over a patient pain pattern at electrical stimulation parameter settings within a first duty cycle range, wherein determining the cathode-minimized configuration of the plurality of electrodes comprises:
    controlling the stimulator device to execute an electrode impedance measurement to determine a set of electrodes of the plurality of electrodes to use to deliver electrical stimulation, wherein the set of electrodes comprises a number of cathodes;
    adjusting a stimulation amplitude of the set of electrodes to induce paresthesia over the patient pain pattern using the set of electrodes; and
    decreasing the initial number of cathodes in the set of electrodes until the set of electrodes comprises a minimum number of cathodes that induces paresthesia over the patient pain pattern;
  output for display instructions for determining electrical stimulation parameter settings within a second duty cycle range for the stimulator device to deliver non-paresthesia inducing electrical stimulation that at least partially suppresses the pain pattern using the cathode-minimized configuration of the plurality of electrodes; and
  transmit data to the stimulator device to program the stimulator device to deliver non-paresthesia inducing electrical stimulation at determined parameter settings within the second duty cycle range using the cathode-minimized configuration of the plurality of electrodes.

* * * * *